(12) United States Patent
During

(10) Patent No.: US 9,801,864 B2
(45) Date of Patent: *Oct. 31, 2017

(54) METHODS OF INCREASING TONIC INHIBITION AND TREATING SECONDARY INSOMNIA

(71) Applicant: Ovid Therapeutics Inc., New York, NY (US)

(72) Inventor: Matthew During, Weston, CT (US)

(73) Assignee: OVID THERAPEUTICS INC, New York, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/375,735

(22) Filed: Dec. 12, 2016

(65) Prior Publication Data

US 2017/0087133 A1 Mar. 30, 2017

Related U.S. Application Data

(63) Continuation of application No. 14/729,910, filed on Jun. 3, 2015, now abandoned.

(60) Provisional application No. 62/008,939, filed on Jun. 6, 2014.

(51) Int. Cl.
| | | |
|---|---|---|
| *A61K 31/437* | (2006.01) | |
| *A61K 9/00* | (2006.01) | |
| *A61K 9/70* | (2006.01) | |

(52) U.S. Cl.
CPC .......... *A61K 31/437* (2013.01); *A61K 9/0053* (2013.01); *A61K 9/0019* (2013.01); *A61K 9/7023* (2013.01)

(58) Field of Classification Search
CPC .. A61K 31/437; A61K 9/0053; A61K 9/0019; A61K 9/7023
USPC ........................................................ 514/302
See application file for complete search history.

(56) References Cited

U.S. PATENT DOCUMENTS

| | | | |
|---|---|---|---|
| 4,278,676 | A | 7/1981 | Krogsgaard-LarsenPovl |
| 4,353,910 | A | 10/1982 | Perregaard |
| 4,362,731 | A | 12/1982 | Hill |
| 5,948,433 | A | 9/1999 | Burton et al. |
| 5,985,311 | A | 11/1999 | Cordes et al. |
| 6,461,644 | B1 | 10/2002 | Jackson et al. |
| 6,676,961 | B1 | 1/2004 | Lichter |
| 9,339,495 | B2 | 5/2016 | During |
| 9,446,028 | B2 | 9/2016 | During |
| 2011/0046090 | A1 | 2/2011 | Barlow et al. |
| 2015/0352085 | A1 | 12/2015 | During |
| 2017/0014393 | A1* | 1/2017 | During ................. A61K 31/437 |

FOREIGN PATENT DOCUMENTS

| | | |
|---|---|---|
| EP | 0000338 A2 | 1/1979 |
| WO | 9702813 A1 | 1/1997 |
| WO | 2005094820 A1 | 10/2005 |

OTHER PUBLICATIONS

Olmos-Serrano et al Developmental Neuroscience, 2011, 33, 395-403.*
Egawa et al. "Decreased Tonic Inhibition in Cerebellar Granule Cells Causes Motor Dysfunction in a Mouse Model of Angelman Syndrome," Science Translational Medicine, 2012, vol. 4, Na 163 (163ra157); 11 pages.
James K. Walsh, Ph.D., "Enhancement of Slow Wave Sleep: Implications for Insomnia," Journal of Clinical Sleep Medicine, Supplement to vol. 5, No. 2 (2009); pp. 827-832.
Wang et al., "Neurobiology of Disease—The Melatonin MT1 Receptor Axis Modulates Mutant Huntingin-Mediated Toxicity," The Journal of Neuroscience 31(41), Oct. 12, 2011; pp. 14496-14507.
Williams et al., "Conference Report—Angelman Syndrome 2005: Updated Consensus for Diagnostic Criteria," American Journal of Medical Genetics 140A (2006); pp. 413-418.
de Die-Smulders et al., "Reproductive Options for Prospective Parents in Families with Huntington's Disease: Clinical, Psychological and Ethical Reflections," Human Reproduction Update, vol. 19, No. 3 (2013); pp. 304-315.
Braat et al., "Fragile X Syndrome Neurobiology Translates Into Rational Therapy," Drug Discovery Today, vol. 00, No. 00, Feb. 2014; pp. 1-10.
International Search Report and Written Opinion of the International Searching Authority, dated Aug. 26, 2015, corresponding to International Application No. PCT/US15/34018; 12 total pages.
Natural Patterns of Sleep—Healthy Sleep—http://healthysleep.med.harvard.edu/healthy/science/what/sleep-pat- terns-rem-nrem (2007); 3 pages.
Waldemar et al., "Recommendations for the Diagnosis and Management of Alzheimer's Disease and other Disorders Associated with Dementia: EFNS Guideline," European Journal of Neurology 14, (2007); pp. e1-e26.

(Continued)

*Primary Examiner* — Yevegeny Valenrod
(74) *Attorney, Agent, or Firm* — Carter, DeLuca, Farrell & Schmidt, LLP

(57) ABSTRACT

Methods of increasing tonic inhibition in a subject in need thereof, for example a subject with Fragile X syndrome or Angelman syndrome are disclosed. Methods of treating secondary insomnia in a subject with a neurodegenerative disease or disorder are also disclosed. The methods can include administering the subject an effective amount of 4,5,6,7-tetrahydroisoxazolo(5,4-c)pyridin-3-ol (THIP) or a derivative thereof, or a pharmaceutically acceptable salt thereof, increase tonic inhibition in neurons of the subject; to increase slow wave sleep (SWS) and/or slow wave activity (SWA), normalize sleep architecture, reduce secondary insomnia, increase non-rapid eye movement (NREM) sleep, increase sleep continuity, enhance delta activity within NREM, increase or improve total sleep time (TST), increase or improve sleep efficiency, reduce total time awake (TAA), reduce number of awakenings (NWA), reduce latency to persistent sleep (LPS), or to reduce wake after sleep onset (WASO), in the subject, or any combination thereof.

6 Claims, No Drawings

(56) References Cited

OTHER PUBLICATIONS

Walsh et al., "The Selective Extrasynaptic GABAA Agonist, Gaboxadol, Improves Traditional Hypnotic Efficacy Measures and Enhances Slow Wave Activity in a Model of Transient Insomnia," Sleep, vol. 30, No. 5, 2007; pp. 593-602.
Walter Alexander, "Sleep: Gaboxadol Enhances Slow Wave Sleep," Perelman, School of Medicine, Jun. 22, 2006; 3 pages.
Bamford et al., "A Prospective Evaluation of Cognitive Decline in Early Huntington's Disease: Functional and Radiographic Correlates," Neuroglogy, 45, Oct. 1995; pp. 1867-1873.
Brooks et al., "El Escorial Revisited: Revised Criteria for the Diagnosis of Amyotrophic Lateral Sclerosis", ALS and Other Motor Neuron Disorders, 2000, 1; pp. 293-299.
Brown et al., "Microarray Identification of FMRP—Associated Brain mRNAs and Altered mRNA Translational Profiles in Fragile X Syndrome," Cell, vol. 107, Nov. 16, 2001; pp. 477-487.
Brown et al., "Pharmacological Characterization of a Novel Cell Line Expressing Human ?4?3? GABAA Receptors," British Journal of Pharmacology, (2002) 136; pp. 965-974.
Castrillo-Viguera et al., Clinical Significance in the Change of Decline in ALSFRS-R, Amyotrophic Lateral Scelerosis, (2010), 11; pp. 178-180.
Sarah DeWeerdt, "Fragile X Mice Show Brain-Wave Abnormalities During Sleep," SFARI, Simons Foundation, Autism Research Initiative, Jan. 25, 2013; 2 pages.
Deacon et al., "Effect of Short-Term Treatment with Gaboxadol on Sleep Maintenance and Initiation in Patients with Primary Insomnia," Sleep, vol. 30, No. 3 (2007); pp. 281-287.
Duyao et al., "Trinucleotide Repeat Length Instability and Age of Onset in Huntington's Disease," Nature Genetics, vol. 1, 1993 Nature Publishing Group, http://www.nature.cominaturegenetics; Aug. 1993; pp. 387-392.
Faulhaber et al., "The GABAA Agonist THIP Produces Slow Wave Sleep and Reduces Spindling Activity in NREM Sleep in Humans," Psychopharmacology, 130, (1997); pp. 285-291.
Fox et al., "Transdermal Drug Delivery Enhancement by Compounds of Natural Origin," Molecules, 16, (2011); pp. 10507-10540.
Gaboxadol, from Wikipedia, the free encylopedia,http://en.wikipedia.orgiwiki/Gaboxadol, 2014; 2 pages.
Gaboxadol, Investigational Agent—Drug Development Technology, http//www.drugdevelopment-technology.com/projects/gaboxadol-2014; 3 pages.
Gaboxadol, Bluelight, http://www.bluelight.org/vb/threads/370965-Gaboxadol—(2014); 1 page.
Glykys et al., "The Main Source of Ambient GABA Responsible for Tonic Inhibition in the Mouse Hippocampus," J Physiol 582.3 (2007); pp. 1163-1178.
Paul H. Gordon, "Amyotrophic Lateral Sclerosis: An Update for 2013 Clinical Features, Pathophysiology, management and Therapeutic Trials," Aging and Disease, vol. 4, No. 5, Oct. 2013; pp. 295-310.
Hajak et al., "A 2-week Efficacy and Safety Study of Gaboxadol and Zolpidem Using Electronic Diaries in Primary Insomnia Outpatients," Sleep Medicine, 10 (2009); pp. 705-712.
Huntington Study Group, "Unified Huntington's Disease Rating Scale: Reliability and Consistency," Movement Disorders, vol. 11, No. 2, 1996; pp. 136-142.
Iber et al., "The AASM Manual for the Scoring of Sleep and Associated Events," American Academy of Sleep Medicine (2007); pp. 3-59.
J. Jankovic, "Parkinson's Disease: Clinical Features and Diagnosis," J. Neural Neurosurg. Psychiatry 79, (2008); pp. 368-376.
Jennum et al., "Sleep Disorders in Neurodegenerative Disorders and Stroke," European Handbook of Neurological Management, vol. 1, 2nd Edition, Chapter 39, Section 6—Sleep Disorders, (Ed. Gilhus et al.) Blackwell Publishing Ltd. 2011; pp. 529-543.
Jonas et al., "Neural Inhibition,", Scholarpedia—http://www.scholarpedia.org/article/Neural.sub.--inhibition---(2014); 10 pages.

Lancel et al., "The GABAA Agonist THIP (Gaboxadol) Increases Non-REM Sleep and Enhances Delta Activity in the Rat," Sleep and Rhythms, NeuroReport, Rapid Science Publishers, vol. 7, No. 13; Sep. 1996; pp. 2241-2245.
Lancel, et al. "The GABAA Agonist THIP Increases Non-REM Sleep and Enhances Non-REM Sleep-Specific Delta Activity in the Rat During the Dark Period," Sleep, vol. 20, No. 12, American Sleep Disorders Association and Sleep Research Society (1997); pp. 1099-1104.
Lancel, "Role of GABAA Receptors in the Regulation of Sleep: Initial Sleep Responses to Peripherally Administered Modulators and Agonists," Sleep, vol. 22, No. 1, (1999); pp. 33-42.
Lancel et al., "Effect of the GABAA Agonist Gaboxadol on Nocturnal Sleep and Hormone Secretion in Healthy Elderly Subjects," Am J. Physiol Endoctrinol Metab 281; (2001), pp. E130-E137.
Larsen et al., "Intestinal Gaboxadol Absorption via PAT1 (SLC36A1): Modified Absorption in vivo Following Co-administration of L-tryptophan," British Journal of Pharmacology (BJP), 157, (2009); pp. 1380-1389.
Lo Coco et al., "Sleep-Wake Problems in Patients with Amyotrophic Lateral Sclerosis: Implications for Patient Management," Neurodegen. Dis. Manage. , 2(3), (2012); pp. 315-324.
Lundahl et al., "Short-term Treatment with Gaboxadol Improves Sleep Maintenance and Enhances Slow Wave Sleep in Adult Patients with Primary Insomnia," Psychopharmacology 195 (2007); pp. 139-146.
Mackenzie et al., "TDP-43 and FUS in Amyotrophic Lateral Sclerosis and Frontotemporal Dementia," Lancet Neurology, vol. 9; (Oct. 2010); pp. 995-1007.
Marshall et al., "Specific Psychiatric Manifestations Among Preclinical Huntington Disease," JAMA Neurology, vol. 64, No. 1, (Jan. 2007), Arch Neurol. 64(1) (2007); pp. 116-121; (10 pages).
Mathias et al., "The GABAA Agonist Gaboxadol Improves the Quality of Post-Nap Sleep," Psychopharmacology 157 (2001); pp. 299-304.
Mathias et al., "Effect of Repeated Gaboxadol Administration on Night Sleep and Next-Day Performance in Healthy Elderly Subjects," Neuropsychopharmacology 30, (2005) pp. 833-841.
Morton, "HDBuzz Special Feature: Huntington's Disease and Sleep," HDBuzz, Huntington's Disease Research News, (2013); 8 pages.
Olmos-Serrano et al, "Defective GABAergic Neurotransmission and Pharmacological Rescue of Neuronal Hyperexcitability in the Amygdala in a Mouse Model of Fragile X Syndrome," The Journal of Neuroscience, Jul. 21, 2010, 30(29), pp. 9929-9938 (pp. 1-25).
Olmos-Serrano et al, "The GABAA Receptor Agonist THIP Ameliorates Specific Behavioral Deficits in the Mouse Model of Fragile X Syndorme," Developmental Neuroscience 33, Fragile X Syndrome/Review, (2011), pp. 395-403.
Pathan et al, "Chemical Penetration Enhancers for Transdermal Drug Delivery Systems," Tropical Journal of Pharmaceutical Research, vol. 8, No. 2 (2009); pp. 173-179.
Rosenberg et al, "Neuropsychological Characteristics of Huntington's Disease Carriers: A Double Blind Study," J Med Genet 32, (1995); pp. 600-604.
Rowland et al, "Amyotrophic Lateral Sclerosis," The New England Journal of Medicine, vol. 344, No. 22, May 31, 2001; pp. 1688-1700.
Stephanie Saul, "Merck Cancels Work on a New Insomnia Medication," The New York Times, Mar. 29, 2007; 2 pages.
Webb, et al., "The frequency of the fragile X chromosome among schoolchildren in Coventry", Journal of Medical Genetics, 1986, vol. 23; pp. 396-399.
Egawa et al., "Pathophysiological power of improper tonic GABA(A) conductances in mature and immature models." Frontiers in Neural Circuits, Oct. 2013, vol. 7, Article 170; pp. 1-15.
Youings, et al., FRAXA and FRAXE: the results of a five year survey. J. Med. Genet. 2000, vol. 37: pp. 415-421.
Crawford, et al., "FMR1 and the Fragile X Syndrome: Human Genome Epidemiology Review," Genet. Med. 2001, vol. 3, No. 5 (Author Manuscript); pp. 359-371.

(56) References Cited

OTHER PUBLICATIONS

Crawford, et al., "Prevalence of the Fragile X Syndrome in African-Americans," American Journal of Medical Genetic (Jul. 1, 2002), vol. 110, Issue 3: pp. 226-233.

Miyashiro et al., "RNA Cargoes Associating with FMRP Reveal Deficits in Cellular Functioning in Fmr1 Null Mice" Neuron, Feb. 6, 2003, vol. 37; pp. 417-431.

Dictenberg et al., "A Direct Role for FMRP in Activity-Dependent Dendritic mRNA Transport Links Filopodial-Spine Morphogenesis to Fragile X Syndrome," Dev Cel (Jun. 2008), vol. 14, No. 6 (Author Manuscript); pp. 926-939.

Braat et al., "The GABAA receptor is an FMRP target with therapeutic potential in fragile X syndrome," Cell Cycle (Sep. 15, 2015) vol. 14, No. 18; pp. 2985-2995.

Braat et al., "Insights into GABAAergic system deficits in fragile X syndrome lead to clinical trials," Neuropharmacology (Jan. 2015), vol. 88; pp. 48-54.

Curia et al., "Downregulation of Tonic GABAergic Inhibition in a Mouse Model of Fragile X Syndrome," Cerebral Cortex (Jul. 2009), vol. 19; pp. 1515-1520.

El Idrissi et al., "Decreased GABA(A) receptor expression in the seizure-prone fragile X mouse," Neurosci Lett (2005) vol. 377, No. 3; pp. 141-146.

Gantois et al., "Expression profiling suggests underexpression of the GABA(A) receptor subunit delta in the fragile X knockout mouse model, " Neurobiol Dis (2006), vol. 21, No. 2; pp. 346-357.

Turner et al., "Preventive Screening for the Fragile X Syndrome," The New England Journal of Medicine (1986), vol. 315, No. 10; pp. 607-609.

Turner et al., "Prevalence of fragile X syndrome," Am. J. Med. Genet. (1996), vol. 64; pp. 196-197.

Martin et al., "Deficient Tonic GABAergic conductance and synaptic balance in the fragile X sydrome amygdala," J. Neurophysiol (May 21, 2014), vol. 112, pp. 890-902.

Coffee et al., "Incidence of Fragile X Syndrome by Newborn Screening for Methylated FMR1 DNA," The American Journal of Human Genetics (Oct. 9, 2009), vol. 85; pp. 503-514.

Lozano et al., "Modulation of the GABAergic pathway fro the treatment of fragile X syndrome", Neuropsychiatric Disease and Treatment (2014), vol. 10 (Dovepress); pp. 1769-1779.

Kazdoba et al, "Modeling fragile X syndrome in the Fmr1 knockout mouse," Intractable & Rare Diseases Research (2014), vol. 3, No. 4; pp. 118-133.

Paluszkiewicz et al., "Fragile X Syndrome: The GABAergic System and Circuit Dysfunction," Developmental Neuroscience (2011); vol. 33; pp. 349-364.

Rio et al., The contribution of inhibitory interneurons to cirecuit dysfunction in Fragile X Syndrome, Froneiers in Cellular Neuroscience (Aug. 25, 2014), vol. 8, Article 245; pp. 1-7.

R. Shiwach, "Psychopathology in Huntington's Disease Patients," Acta Psychiatr Scand 90, (1994); pp. 241-246.

Tropea et al., "Partial Reversal of Rett Syndrome-like Symptoms in MeCP2 Mutant Mice," PNAS, vol. 106, No. 6, Feb. 10, 2009; pp. 2029-2034.

Videnovic et al.., "Circadian Melatoni Rhythm and Excessive Daytime Sleepiness in Parkinson Disease Free," JAMA Neurol. 71(4), 2014; Original Investigation—2014; pp. 463-469 (12 pages).

Francis O Walker, Huntington's Disease, Seminar, Lancet, vol. 369, (Jan. 20, 2007); pp. 218-228.

* cited by examiner

METHODS OF INCREASING TONIC INHIBITION AND TREATING SECONDARY INSOMNIA

CROSS REFERENCE TO RELATED APPLICATION

This application claims benefit of and priority to U.S. Provisional Application No. 62/008,939, filed Jun. 6, 2014, all of which is incorporated by reference in its entirety.

FIELD OF THE INVENTION

The field of the invention generally relates to methods of using a composition including 4,5,6,7-tetrahydroisoxazolo (5,4-c)pyridin-3-ol (THIP), a derivative thereof, or a pharmaceutically acceptable salt thereof for treating diseases and disorders characterized by secondary insomnia and/or defects or deficiencies in tonic inhibition.

BACKGROUND OF THE INVENTION

Although many advances have been made, the treatments for neurodegenerative diseases and neurogenetic diseases remain largely inadequate.

In some cases, neurological diseases are linked by an underlying pathophysiology, for example, Fragile X syndrome and Angelman syndrome are linked by loss of tonic inhibition in certain tissues of the brain. In some cases, neurological diseases are linked by symptoms. For example, although different neurodegenerative diseases are characterized by a broad range of symptoms, many of the diseases and disorders are linked by one or more sleep-related disorders, such as insomnia, disrupted sleep, and altered sleep architecture (Jennum, et al., "CHAPTER 39: Sleep disorders in neurodegenerative disorders and stroke", *European Handbook of Neurological Management*, Volume 1, 2nd Edition (Ed. Gilhus, et al.) Blackwell Publishing Ltd. 2011)).

For diseases such as Huntington's disease, Parkinson's disease, Amyotrophic Lateral Sclerosis, Alzheimer's disease, Fragile X syndrome, and Angelman syndrome, treatments are very limited and cures do not exist. Therefore, there is a need for additional therapeutic options for treating neurodegenerative diseases, neurogenetic, and other central nervous system disorders.

Accordingly, it is an object of the invention to provide methods for treating and preventing secondary insomnia in subjects with neurological diseases.

It is another object of the invention to provide methods for increasing tonic inhibition in a subject in need thereof.

SUMMARY OF THE INVENTION

Methods of increasing tonic inhibition of neurons in a subject, particularly subjects with Fragile X syndrome or Angelman syndrome are provided. Methods of treating secondary insomnia in a subject with a neurodegenerative disease or a central nervous system disorder are also provided. The methods typically include administering to the subject a pharmaceutical composition including an effective amount of 4,5,6,7-tetrahydroisoxazolo(5,4-c)pyridin-3-ol (THIP) or a derivative thereof and a pharmaceutically acceptable carrier or excipient to increase tonic inhibition of neurons in the subject, to increase slow wave sleep (SWS) and/or slow wave activity (SWA), normalize sleep architecture, reduce secondary insomnia, increase non-rapid eye movement (NREM) sleep, increase sleep continuity, enhance delta activity within NREM, increase or improve total sleep time (TST), increase or improve sleep efficiency, reduce total time awake (TAA), reduce number of awakenings (NWA), reduce latency to persistent sleep (LPS), or reduce wake after sleep onset (WASO) in the subject, or any combination thereof in the subject.

In particular embodiments, the subjects suffering from secondary insomnia have Parkinson's Disease (PD) or a PD-related disorder, Alzheimer's Disease (AD), Huntington's disease, Parkinson's disease, Amyotrophic lateral sclerosis, or Alzheimer's disease.

In the most preferred embodiments, the THIP or derivative thereof is THIP or a pharmaceutically acceptable salt thereof. The THIP or derivative thereof can be the singular active agent or one of two or more active agents in the pharmaceutical composition. The pharmaceutical composition is formulated for extended release. The pharmaceutical composition can be administered transdermally, for example, by contacting a transdermal patch including the pharmaceutical composition with the skin of the subject. In a particular embodiment, the daily dosage of the THIP or derivative thereof is between about 2.5 mg and 50 mg per day.

DETAILED DESCRIPTION OF THE INVENTION

I. Definitions

As used herein, the term "carrier" or "excipient" refers to an organic or inorganic ingredient, natural or synthetic inactive ingredient in a formulation, with which one or more active ingredients are combined.

As used herein, the term "pharmaceutically acceptable" means a nontoxic material that does not interfere with the effectiveness of the biological activity of the active ingredients.

As used herein, the terms "effective amount" or "therapeutically effective amount" means a dosage sufficient to alleviate one or more symptoms of a disorder, disease, or condition being treated, or to otherwise provide a desired pharmacologic and/or physiologic effect. The precise dosage will vary according to a variety of factors such as subject-dependent variables (e.g., age, immune system health, etc.), the disease or disorder being treated, as well as the route of administration and the pharmacokinetics of the agent being administered.

As used herein, the term "prevention" or "preventing" means to administer a composition to a subject or a system at risk for or having a predisposition for one or more symptom caused by a disease or disorder to cause cessation of a particular symptom of the disease or disorder, a reduction or prevention of one or more symptoms of the disease or disorder, a reduction in the severity of the disease or disorder, the complete ablation of the disease or disorder, stabilization or delay of the development or progression of the disease or disorder.

II. Compositions Including Gaboxadol or a Derivative Thereof

Methods of using 4,5,6,7-tetrahydroisoxazolo(5,4-c)pyridin-3-ol (THIP), a derivative thereof, or a pharmaceutically acceptable salt thereof for treating secondary insomnia, disturbed sleep architecture, or a combination thereof in a subject are disclosed. In some embodiments, the subject has or is at risk of developing a neurodegenerative disease or a central nervous system disorder. In the most preferred embodiments, the subject suffers from secondary insomnia and/or disturbed sleep architecture due to a neurodegenerative disease or a central nervous system disorder. As discussed in more detail below, the methods typically include administering to a subject in need thereof an effective amount of 4,5,6,7-tetrahydroisoxazolo(5,4-c)pyridin-3-ol (THIP), a derivative thereof, or a pharmaceutically acceptable salt thereof to increase slow wave sleep, normalize sleep architecture, or a combination thereof a subject. In some embodiments, clinical symptoms of a neurodegenerative disease or central nervous system disorder are reduced.

Methods of using 4,5,6,7-tetrahydroisoxazolo(5,4-c)pyridin-3-ol (THIP), a derivative thereof, or a pharmaceutically acceptable salt thereof for increasing tonic inhibition are also provided. The methods can be used to increase tonic inhibition in a subject with a disease or disorder characterized a defect or deficiency in tonic inhibition, for example Fragile X Syndrome or Angelman Syndrome.

A. 4,5,6,7-tetrahydroisoxazolo(5,4-c)pyridin-3-ol (THIP)

The compositions for use in the disclosed methods of treating secondary insomnia include 4,5,6,7-tetrahydroisoxazolo(5,4-c)pyridin-3-ol (also referred to as THIP and gaboxadol), a derivative thereof, or pharmaceutically acceptable salt thereof, or a structurally related compound. THIP, as well as derivatives and structurally related compounds, and methods of making thereof are known in the art. See, for example, U.S. Pat. Nos. 4,278,676, 4,362,731, 4,353,910, and WO 2005/094820 each of which is specifically incorporated by reference herein in its entirety. Particularly preferred compounds are discussed in more detail below.

In some embodiments, the compound is of the formula Ia

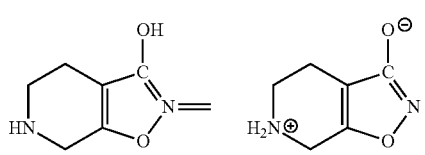

4,5,6,7-tetrahydroisoxazolo(5,4-c)pyridin-3-ol (THIP)

or a tautomer, isomer, epimer, or diastereoisomer thereof.

THIP is well tolerated and is a very potent GABA agonist having a very specific activity, and being inactive as a GABA-uptake inhibitor. Gaboxadol is a selective extrasynaptic $GABA_A$ agonist (SEGA) (Deacon, et al., *Sleep*, 30(3): 281-287 (2007)). The $GABA_A$ receptor is a pentameric transmembrane protein that has 5 subunits forming a central anion channel. Gaboxadol binds at the interface between the α and β subunits, the same site to which the endogenous GABA ligand binds. Gaboxadol exerts direct effects on chloride conductance, independent of GABA and it can directly activate extrasynaptically located δ-containing receptors via interaction with the GABA binding site. Extrasynaptic δ-containing receptors are predominantly expressed in the thalamus, cerebral cortex, and limbic system. These regions of the brain have been implicated in sleep regulation and synchronization of cortical activity.

It is believed that the selective activity of the compound Ia is ascribable to the particular position of the nitrogen atom in the 6-membered ring in relation to the acidic hydroxy group in the 5-membered ring.

Therefore, compound Ia and derivatives thereof, particularly derivatives which upon administration will be decomposed in situ to yield the parent compound Ia, in particular compounds of the general formula I

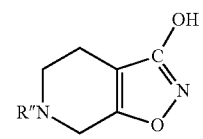

wherein R" is hydrogen, acetyl or a group of the general formula II

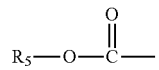

wherein $R_5$ is $C_{1-8}$ alkyl; phenyl; phenyl substituted in the 4-position with halogen, lower alkoxy, or lower alkyl; or phenylalkyl such as benzyl or phenylethyl in which the phenyl group may be substituted in the 4-position with halogen, lower alkoxy, or lower alkyl; and salts thereof.

It is believed that the groups R" which are different from hydrogen may enhance the penetration of the compounds into the brain in that they may enhance the ability of the compounds to pass the blood brain barrier, and will thereafter be split off in situ to yield the parent compound. Also, a prolonged effect of Ia may be obtained via decomposition in situ of compounds wherein R" is different from hydrogen, to yield the parent compound.

"Lower alkyl", "lower alkoxy", and "lower alkyloxy" designate such groups containing 1-6 carbon atoms, preferably 1-4 atoms inclusive.

The compounds of the general formula I may exist in a tautomeric form, as shown by the formula I'

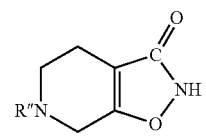

Formula I is to be understood as covering also this tautomeric form (I') and mixtures of the two tautomeric forms.

Examples of compounds of the general formula I in which R" is different from hydrogen, are: 6-acetyl-4,5,6,7-tetrahydroisoxazolo[5,4-c]pyridine-3-ol, methyl 3-hydroxy-4,5,6,7-tetrahydroisoxazolo[5,4-c]pyridine-6-carboxylate, ethyl 3-hydroxy-4,5,6,7-tetrahydroisoxazolo[5,4-c]pyridine-6-carboxylate, tert.butyl 3-hydroxy-4,5,6,7-tetrahydroisoxazolo[5,4-c]pyridine-6-carboxylate, phenyl 3-hydroxy-4,5,6,7-tetrahydroisoxazolo[5,4-c]pyridine-6-carboxylate, 4-chlorophenyl 3-hydroxy-4,5,6,7-tetrahydroisoxazolo[5,4-c]pyridine-6-carboxylate, 4-methoxyphenyl 3-hydroxy-4,5,6,7-tetrahydroisoxazolo[5,4-c]pyridine-6-carboxylate, benzyl 3-hydroxy-4,5,6,7-tetrahydroisoxazolo[5,4-c]pyridine-6-carboxylate, and salts thereof with bases.

Derivatives of THIP are known in the art. See, for examples, U.S. Pat. No. 4,353,910.

Preferred derivatives have the formula

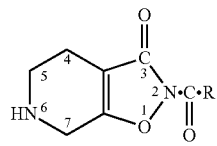

wherein R is an alkyl group, branched or unbranched, having from one to seventeen carbon atoms inclusive, a phenyl group optionally substituted with one or two groups selected from lower alkyl, lower alkyloxy and halogen, a phenylalkyl group, lower alkyloxy group or a —$NHR_1$ group, wherein $R_1$ is hydrogen, lower alkyl, phenyl or cyclohexyl, as well as pharmaceutically acceptable acid addition salts thereof.

Formula III as well as their pharmaceutically acceptable acid addition salts show GABA-related activity at the same level as does the compound THIP, and some of the compounds also show a prolonged effect compared with THIP. They moreover show pronounced analgesic and myotonolytic effects.

As examples of pharmaceutically acceptable salts of the compounds of the disclosed formulae may be mentioned salts with inorganic acids. Examples of salts of the compounds of the formulae are acid addition salts thereof, such as pharmaceutically acceptable salts with inorganic acids, e.g. hydrochloric, hydrobromic, nitric, sulfuric, phosphoric acids and the like, or with organic acids, such as organic carboxylic acids, e.g. acetic, propionic, glycolic, malonic, succinic, maleic, fumaric, malic, tartaric, citric, glucuronic, benzoic, pamoic acid and the like, or organic sulfonic acids, e.g. methane sulfonic, ethane sulfonic, benzene sulfonic, toluene sulfonic acid and the like, which salts may be prepared by procedures known per se, e.g. by adding the acid in question to the base, preferably in a solvent. Compounds of the formulae can form pharmaceutically acceptable salts with bases, such as metal salts, e.g. sodium, potassium, calcium or aluminium salts, and ammonium and substituted ammonium salts, e.g. salts of amines such as triethylamine, triethanolamine, ethylpiperidine, procaine, and dibenzylamine.

Throughout the description "THIP or a derivative thereof" is intended to include any form of the compound, such as the base (zwitter ion), pharmaceutically acceptable salts, e.g., pharmaceutically acceptable acid addition salts, hydrates or solvates of the base or salt, as well as anhydrates, and also amorphous, or crystalline forms.

B. Formulations

The disclosed compounds can be formulated in a pharmaceutical composition. Pharmaceutical compositions can be for administration by parenteral (intramuscular, intraperitoneal, intravenous (IV) or subcutaneous injection), enteral, transdermal (either passively or using iontophoresis or electroporation), or transmucosal (nasal, pulmonary, vaginal, rectal, or sublingual) routes of administration or using bioerodible inserts and can be formulated in dosage forms appropriate for each route of administration.

The compositions can be administered systemically.

Drugs can be formulated for immediate release, extended release, or modified release. A delayed release dosage form is one that releases a drug (or drugs) at a time other than promptly after administration. An extended release dosage form is one that allows at least a twofold reduction in dosing frequency as compared to that drug presented as a conventional dosage form (e.g. as a solution or prompt drug-releasing, conventional solid dosage form). A modified release dosage form is one for which the drug release characteristics of time course and/or location are chosen to accomplish therapeutic or convenience objectives not offered by conventional dosage forms such as solutions, ointments, or promptly dissolving dosage forms. Delayed release and extended release dosage forms and their combinations are types of modified release dosage forms.

Formulations are prepared using a pharmaceutically acceptable "carrier" composed of materials that are considered safe and effective and may be administered to an individual without causing undesirable biological side effects or unwanted interactions. The "carrier" is all components present in the pharmaceutical formulation other than the active ingredient or ingredients. The term "carrier" includes, but is not limited to, diluents, binders, lubricants, desintegrators, fillers, and coating compositions.

"Carrier" also includes all components of the coating composition which may include plasticizers, pigments, colorants, stabilizing agents, and glidants. The delayed release dosage formulations may be prepared as described in references such as "Pharmaceutical dosage form tablets", eds. Liberman et. al. (New York, Marcel Dekker, Inc., 1989), "Remington—The science and practice of pharmacy", 20th ed., Lippincott Williams & Wilkins, Baltimore, Md., 2000, and "Pharmaceutical dosage forms and drug delivery systems", 6th Edition, Ansel et. al., (Media, Pa.: Williams and Wilkins, 1995) which provides information on carriers, materials, equipment and process for preparing tablets and capsules and delayed release dosage forms of tablets, capsules, and granules.

The compound can be administered to a subject with or without the aid of a delivery vehicle. Appropriate delivery vehicles for the compounds are known in the art and can be selected to suit the particular active agent. For example, in some embodiments, the active agent(s) is incorporated into or encapsulated by, or bound to, a nanoparticle, microparticle, micelle, synthetic lipoprotein particle, or carbon nanotube. For example, the compositions can be incorporated into a vehicle such as polymeric microparticles which provide controlled release of the active agent(s). In some embodiments, release of the drug(s) is controlled by diffusion of the active agent(s) out of the microparticles and/or degradation of the polymeric particles by hydrolysis and/or enzymatic degradation.

Suitable polymers include ethylcellulose and other natural or synthetic cellulose derivatives. Polymers which are slowly soluble and form a gel in an aqueous environment, such as hydroxypropyl methylcellulose or polyethylene oxide, may also be suitable as materials for drug containing microparticles or particles. Other polymers include, but are not limited to, polyanhydrides, poly (ester anhydrides), polyhydroxy acids, such as polylactide (PLA), polyglycolide (PGA), poly(lactide-co-glycolide) (PLGA), poly-3-hydroxybut rate (PHB) and copolymers thereof, poly-4-hydroxybutyrate (P4HB) and copolymers thereof, polycaprolactone and copolymers thereof, and combinations thereof. In some embodiments, both agents are incorporated into the same particles and are formulated for release at different times and/or over different time periods. For example, in some embodiments, one of the agents is released entirely from the particles before release of the second agent begins. In other embodiments, release of the first agent begins followed by release of the second agent before the all of the first agent is released. In still other embodiments, both agents are released at the same time over the same period of time or over different periods of time.

1. Formulations for Parenteral Administration

Compounds and pharmaceutical compositions thereof can be administered in an aqueous solution, by parenteral injection. The formulation may also be in the form of a suspension or emulsion. In general, pharmaceutical compositions are provided including effective amounts of the active agent(s) and optionally include pharmaceutically acceptable diluents, preservatives, solubilizers, emulsifiers, adjuvants and/or carriers. Such compositions include diluents sterile water, buffered saline of various buffer content (e.g., Tris-HCl, acetate, phosphate), pH and ionic strength; and optionally, additives such as detergents and solubilizing agents (e.g., TWEEN® 20, TWEEN® 80 also referred to as POLYSORBATE® 20 or 80), anti-oxidants (e.g., ascorbic acid, sodium metabisulfite), and preservatives (e.g., Thimersol, benzyl alcohol) and bulking substances (e.g., lactose, mannitol). Examples of non-aqueous solvents or vehicles are propylene glycol, polyethylene glycol, vegetable oils, such as olive oil and corn oil, gelatin, and injectable organic esters such as ethyl oleate. The formulations may be lyophilized and redissolved/resuspended immediately before use. The formulation may be sterilized by, for example, filtration through a bacteria retaining filter, by incorporating sterilizing agents into the compositions, by irradiating the compositions, or by heating the compositions.

2. Oral Immediate Release Formulations

Suitable oral dosage forms include tablets, capsules, solutions, suspensions, syrups, and lozenges. Tablets can be made using compression or molding techniques well known in the art. Gelatin or non-gelatin capsules can prepared as hard or soft capsule shells, which can encapsulate liquid, solid, and semi-solid fill materials, using techniques well known in the art.

Examples of suitable coating materials include, but are not limited to, cellulose polymers such as cellulose acetate phthalate, hydroxypropyl cellulose, hydroxypropyl methylcellulose, hydroxypropyl methylcellulose phthalate and hydroxypropyl methylcellulose acetate succinate; polyvinyl acetate phthalate, acrylic acid polymers and copolymers, and methacrylic resins that are commercially available under the trade name Eudragit® (Roth Pharma, Westerstadt, Germany), Zein, shellac, and polysaccharides.

Additionally, the coating material may contain conventional carriers such as plasticizers, pigments, colorants, glidants, stabilization agents, pore formers and surfactants.

Optional pharmaceutically acceptable excipients present in the drug-containing tablets, beads, granules or particles include, but are not limited to, diluents, binders, lubricants, disintegrants, colorants, stabilizers, and surfactants.

Diluents, also termed "fillers," are typically necessary to increase the bulk of a solid dosage form so that a practical size is provided for compression of tablets or formation of beads and granules. Suitable diluents include, but are not limited to, dicalcium phosphate dihydrate, calcium sulfate, lactose, sucrose, mannitol, sorbitol, cellulose, microcrystalline cellulose, kaolin, sodium chloride, dry starch, hydrolyzed starches, pregelatinized starch, silicone dioxide, titanium oxide, magnesium aluminum silicate and powder sugar.

Binders are used to impart cohesive qualities to a solid dosage formulation, and thus ensure that a tablet or bead or granule remains intact after the formation of the dosage forms. Suitable binder materials include, but are not limited to, starch, pregelatinized starch, gelatin, sugars (including sucrose, glucose, dextrose, lactose and sorbitol), polyethylene glycol, waxes, natural and synthetic gums such as acacia, tragacanth, sodium alginate, cellulose, including hydorxypropylmethylcellulose, hydroxypropylcellulose, ethylcellulose, and veegum, and synthetic polymers such as acrylic acid and methacrylic acid copolymers, methacrylic acid copolymers, methyl methacrylate copolymers, aminoalkyl methacrylate copolymers, polyacrylic acid/polymethacrylic acid and polyvinylpyrrolidone.

Lubricants are used to facilitate tablet manufacture. Examples of suitable lubricants include, but are not limited to, magnesium stearate, calcium stearate, stearic acid, glycerol behenate, polyethylene glycol, talc, and mineral oil.

Disintegrants are used to facilitate dosage form disintegration or "breakup" after administration, and generally include, but are not limited to, starch, sodium starch glycolate, sodium carboxymethyl starch, sodium carboxymethylcellulose, hydroxypropyl cellulose, pregelatinized starch, clays, cellulose, alginine, gums or cross linked polymers, such as cross-linked PVP (Polyplasdone XL from GAF Chemical Corp).

Stabilizers are used to inhibit or retard drug decomposition reactions which include, by way of example, oxidative reactions.

Surfactants may be anionic, cationic, amphoteric or nonionic surface active agents. Suitable anionic surfactants include, but are not limited to, those containing carboxylate, sulfonate and sulfate ions. Examples of anionic surfactants include sodium, potassium, ammonium of long chain alkyl sulfonates and alkyl aryl sulfonates such as sodium dodecylbenzene sulfonate; dialkyl sodium sulfosuccinates, such as sodium dodecylbenzene sulfonate; dialkyl sodium sulfosuccinates, such as sodium bis-(2-ethylthioxyl)-sulfosuccinate; and alkyl sulfates such as sodium lauryl sulfate. Cationic surfactants include, but are not limited to, quaternary ammonium compounds such as benzalkonium chloride, benzethonium chloride, cetrimonium bromide, stearyl dimethylbenzyl ammonium chloride, polyoxyethylene and coconut amine. Examples of nonionic surfactants include ethylene glycol monostearate, propylene glycol myristate, glyceryl monostearate, glyceryl stearate, polyglyceryl-4-oleate, sorbitan acylate, sucrose acylate, PEG-150 laurate, PEG-400 monolaurate, polyoxyethylene monolaurate, polysorbates, polyoxyethylene octylphenylether, PEG-1000 cetyl ether, polyoxyethylene tridecyl ether, polypropylene glycol butyl ether, POLOXAMER® 401, stearoyl monoisopropanolamide, and polyoxyethylene hydrogenated tallow amide. Examples of amphoteric surfactants include sodium N-dodecyl-.beta.-alanine, sodium N-lauryl-.beta.-iminodipropionate, myristoamphoacetate, lauryl betaine and lauryl sulfobetaine.

If desired, the tablets, beads granules or particles may also contain minor amount of nontoxic auxiliary substances such as wetting or emulsifying agents, dyes, pH buffering agents, and preservatives.

3. Extended Release Dosage Forms

The extended release formulations are generally prepared as diffusion or osmotic systems, for example, as described in "Remington—The science and practice of pharmacy" (20th ed., Lippincott Williams & Wilkins, Baltimore, Md., 2000). A diffusion system typically consists of two types of devices, reservoir and matrix, and is well known and described in the art. The matrix devices are generally prepared by compressing the drug with a slowly dissolving polymer carrier into a tablet form. The three major types of materials used in the preparation of matrix devices are insoluble plastics, hydrophilic polymers, and fatty compounds. Plastic matrices include, but not limited to, methyl acrylate-methyl methacrylate, polyvinyl chloride, and polyethylene. Hydrophilic polymers include, but are not limited to, methylcellulose, hydroxypropylcellulose, hydroxypropylmethylcellulose, sodium carboxymethylcellulose, and carbopol 934, polyethylene oxides. Fatty compounds include, but are not limited to, various waxes such as carnauba wax and glyceryl tristearate.

Alternatively, extended release formulations can be prepared using osmotic systems or by applying a semi-permeable coating to the dosage form. In the latter case, the desired drug release profile can be achieved by combining low permeable and high permeable coating materials in suitable proportion.

The devices with different drug release mechanisms described above could be combined in a final dosage form comprising single or multiple units. Examples of multiple units include multilayer tablets, capsules containing tablets, beads, granules, etc.

An immediate release portion can be added to the extended release system by means of either applying an immediate release layer on top of the extended release core using coating or compression process or in a multiple unit system such as a capsule containing extended and immediate release beads.

Extended release tablets containing hydrophilic polymers are prepared by techniques commonly known in the art such as direct compression, wet granulation, or dry granulation processes. Their formulations usually incorporate polymers, diluents, binders, and lubricants as well as the active pharmaceutical ingredient. The usual diluents include inert powdered substances such as any of many different kinds of starch, powdered cellulose, especially crystalline and microcrystalline cellulose, sugars such as fructose, mannitol and sucrose, grain flours and similar edible powders. Typical diluents include, for example, various types of starch, lactose, mannitol, kaolin, calcium phosphate or sulfate, inorganic salts such as sodium chloride and powdered sugar. Powdered cellulose derivatives are also useful. Typical tablet binders include substances such as starch, gelatin and sugars such as lactose, fructose, and glucose. Natural and synthetic gums, including acacia, alginates, methylcellulose, and polyvinylpyrrolidine can also be used. Polyethylene glycol, hydrophilic polymers, ethylcellulose and waxes can also serve as binders. A lubricant is necessary in a tablet formulation to prevent the tablet and punches from sticking in the die. The lubricant is chosen from such slippery solids as talc, magnesium and calcium stearate, stearic acid and hydrogenated vegetable oils.

Extended release tablets containing wax materials are generally prepared using methods known in the art such as a direct blend method, a congealing method, and an aqueous dispersion method. In a congealing method, the drug is mixed with a wax material and either spray-congealed or congealed and screened and processed.

4. Delayed Release Dosage Forms

Delayed release formulations are created by coating a solid dosage form with a film of a polymer which is insoluble in the acid environment of the stomach, and soluble in the neutral environment of small intestines.

The delayed release dosage units can be prepared, for example, by coating a drug or a drug-containing composition with a selected coating material. The drug-containing composition may be, e.g., a tablet for incorporation into a capsule, a tablet for use as an inner core in a "coated core" dosage form, or a plurality of drug-containing beads, particles or granules, for incorporation into either a tablet or capsule. Preferred coating materials include bioerodible, gradually hydrolyzable, gradually water-soluble, and/or enzymatically degradable polymers, and may be conventional "enteric" polymers. Enteric polymers, as will be appreciated by those skilled in the art, become soluble in the higher pH environment of the lower gastrointestinal tract or slowly erode as the dosage form passes through the gastrointestinal tract, while enzymatically degradable polymers are degraded by bacterial enzymes present in the lower gastrointestinal tract, particularly in the colon. Suitable coating materials for effecting delayed release include, but are not limited to, cellulosic polymers such as hydroxypropyl cellulose, hydroxyethyl cellulose, hydroxymethyl cellulose, hydroxypropyl methyl cellulose, hydroxypropyl methyl cellulose acetate succinate, hydroxypropylmethyl cellulose phthalate, methylcellulose, ethyl cellulose, cellulose acetate, cellulose acetate phthalate, cellulose acetate trimellitate and carboxymethylcellulose sodium; acrylic acid polymers and copolymers, preferably formed from acrylic acid, methacrylic acid, methyl acrylate, ethyl acrylate, methyl methacrylate and/or ethyl methacrylate, and other methacrylic resins that are commercially available under the tradename EUDRAGIT®. (Rohm Pharma; Westerstadt, Germany), including EUDRAGIT®. L30D-55 and L100-55 (soluble at pH 5.5 and above), EUDRAGIT®. L-100 (soluble at pH 6.0 and above), EUDRAGIT®. S (soluble at pH 7.0 and above, as a result of a higher degree of esterification), and EUDRAGITS®. NE, RL and RS (water-insoluble polymers having different degrees of permeability and expandability); vinyl polymers and copolymers such as polyvinyl pyrrolidone, vinyl acetate, vinylacetate phthalate, vinylacetate crotonic acid copolymer, and ethylene-vinyl acetate copolymer; enzymatically degradable polymers such as azo polymers, pectin, chitosan, amylose and guar gum; zein and shellac. Combinations of different coating materials may also be used. Multi-layer coatings using different polymers may also be applied.

The preferred coating weights for particular coating materials may be readily determined by those skilled in the art by evaluating individual release profiles for tablets, beads and granules prepared with different quantities of various coating materials. It is the combination of materials, method and form of application that produce the desired release characteristics, which one can determine only from the clinical studies.

The coating composition may include conventional additives, such as plasticizers, pigments, colorants, stabilizing agents, glidants, etc. A plasticizer is normally present to reduce the fragility of the coating, and will generally represent about 10 wt. % to 50 wt. % relative to the dry weight of the polymer. Examples of typical plasticizers include polyethylene glycol, propylene glycol, triacetin, dimethyl phthalate, diethyl phthalate, dibutyl phthalate, dibutyl sebacate, triethyl citrate, tributyl citrate, triethyl acetyl citrate, castor oil and acetylated monoglycerides. A stabilizing agent is preferably used to stabilize particles in the dispersion. Typical stabilizing agents are nonionic emulsifiers such as sorbitan esters, polysorbates and polyvinylpyrrolidone. Glidants are recommended to reduce sticking effects during film formation and drying, and will generally represent approximately 25 wt. % to 100 wt. % of the polymer weight in the coating solution. One effective glidant is talc. Other glidants such as magnesium stearate and glycerol monostearates may also be used. Pigments such as titanium dioxide may also be used. Small quantities of an anti-foaming agent, such as a silicone (e.g., simethicone), may also be added to the coating composition.

Methods of Manufacturing

As will be appreciated by those skilled in the art and as described in the pertinent texts and literature, a number of methods are available for preparing drug-containing tablets, beads, granules or particles that provide a variety of drug release profiles. Such methods include, but are not limited to, the following: coating a drug or drug-containing composition with an appropriate coating material, typically although not necessarily incorporating a polymeric material, increasing drug particle size, placing the drug within a matrix, and forming complexes of the drug with a suitable complexing agent.

The delayed release dosage units may be coated with the delayed release polymer coating using conventional techniques, e.g., using a conventional coating pan, an airless spray technique, fluidized bed coating equipment (with or without a Wurster insert). For detailed information concerning materials, equipment and processes for preparing tablets and delayed release dosage forms, see Pharmaceutical Dosage Forms: Tablets, eds. Lieberman et al. (New York: Marcel Dekker, Inc., 1989), and Ansel et al., Pharmaceutical Dosage Forms and Drug Delivery Systems, 6.sup.th Ed. (Media, Pa.: Williams & Wilkins, 1995).

A preferred method for preparing extended release tablets is by compressing a drug-containing blend, e.g., blend of granules, prepared using a direct blend, wet-granulation, or dry-granulation process. Extended release tablets may also be molded rather than compressed, starting with a moist material containing a suitable water-soluble lubricant. However, tablets are preferably manufactured using compression rather than molding. A preferred method for forming extended release drug-containing blend is to mix drug particles directly with one or more excipients such as diluents (or fillers), binders, disintegrants, lubricants, glidants, and colorants. As an alternative to direct blending, a drug-containing blend may be prepared by using wet-granulation or dry-granulation processes. Beads containing the active agent may also be prepared by any one of a number of conventional techniques, typically starting from a fluid dispersion. For example, a typical method for preparing drug-containing beads involves dispersing or dissolving the active agent in a coating suspension or solution containing pharmaceutical excipients such as polyvinylpyrrolidone, methylcellulose, talc, metallic stearates, silicone dioxide, plasticizers or the like. The admixture is used to coat a bead core such as a sugar sphere (or so-called "non-pareil") having a size of approximately 60 to 20 mesh.

An alternative procedure for preparing drug beads is by blending drug with one or more pharmaceutically acceptable excipients, such as microcrystalline cellulose, lactose, cellulose, polyvinyl pyrrolidone, talc, magnesium stearate, a disintegrant, etc., extruding the blend, spheronizing the extrudate, drying and optionally coating to form the immediate release beads.

5. Formulations for Mucosal and Pulmonary Administration

Active agent(s) and compositions thereof can be formulated for pulmonary or mucosal administration. The administration can include delivery of the composition to the lungs, nasal, oral (sublingual, buccal), vaginal, or rectal mucosa. In a particular embodiment, the composition is formulated for and delivered to the subject sublingually.

In one embodiment, the compounds are formulated for pulmonary delivery, such as intranasal administration or oral inhalation. The respiratory tract is the structure involved in the exchange of gases between the atmosphere and the blood stream. The lungs are branching structures ultimately ending with the alveoli where the exchange of gases occurs. The alveolar surface area is the largest in the respiratory system and is where drug absorption occurs. The alveoli are covered by a thin epithelium without cilia or a mucus blanket and secrete surfactant phospholipids. The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchiole, which then lead to the ultimate respiratory zone, the alveoli, or deep lung. The deep lung, or alveoli, is the primary target of inhaled therapeutic aerosols for systemic drug delivery.

Pulmonary administration of therapeutic compositions comprised of low molecular weight drugs has been observed, for example, beta-androgenic antagonists to treat asthma. Other therapeutic agents that are active in the lungs have been administered systemically and targeted via pulmonary absorption. Nasal delivery is considered to be a promising technique for administration of therapeutics for the following reasons: the nose has a large surface area available for drug absorption due to the coverage of the epithelial surface by numerous microvilli, the subepithelial layer is highly vascularized, the venous blood from the nose passes directly into the systemic circulation and therefore avoids the loss of drug by first-pass metabolism in the liver, it offers lower doses, more rapid attainment of therapeutic blood levels, quicker onset of pharmacological activity, fewer side effects, high total blood flow per $cm^3$, porous endothelial basement membrane, and it is easily accessible.

The term aerosol as used herein refers to any preparation of a fine mist of particles, which can be in solution or a suspension, whether or not it is produced using a propellant. Aerosols can be produced using standard techniques, such as ultrasonication or high-pressure treatment.

Carriers for pulmonary formulations can be divided into those for dry powder formulations and for administration as solutions. Aerosols for the delivery of therapeutic agents to the respiratory tract are known in the art. For administration via the upper respiratory tract, the formulation can be formulated into a solution, e.g., water or isotonic saline, buffered or un-buffered, or as a suspension, for intranasal administration as drops or as a spray. Preferably, such solutions or suspensions are isotonic relative to nasal secretions and of about the same pH, ranging e.g., from about pH 4.0 to about pH 7.4 or, from pH 6.0 to pH 7.0. Buffers should be physiologically compatible and include, simply by way of example, phosphate buffers. For example, a representative nasal decongestant is described as being buffered to a pH of about 6.2. One skilled in the art can readily determine a suitable saline content and pH for an innocuous aqueous solution for nasal and/or upper respiratory administration.

Preferably, the aqueous solution is water, physiologically acceptable aqueous solutions containing salts and/or buffers, such as phosphate buffered saline (PBS), or any other aqueous solution acceptable for administration to an animal or human. Such solutions are well known to a person skilled in the art and include, but are not limited to, distilled water, de-ionized water, pure or ultrapure water, saline, phosphate-buffered saline (PBS). Other suitable aqueous vehicles include, but are not limited to, Ringer's solution and isotonic sodium chloride. Aqueous suspensions may include suspending agents such as cellulose derivatives, sodium alginate, polyvinyl-pyrrolidone and gum tragacanth, and a wetting agent such as lecithin. Suitable preservatives for aqueous suspensions include ethyl and n-propyl p-hydroxybenzoate.

In another embodiment, solvents that are low toxicity organic (i.e. nonaqueous) class 3 residual solvents, such as ethanol, acetone, ethyl acetate, tetrahydrofuran, ethyl ether, and propanol may be used for the formulations. The solvent is selected based on its ability to readily aerosolize the formulation. The solvent should not detrimentally react with the compounds. An appropriate solvent should be used that dissolves the compounds or forms a suspension of the compounds. The solvent should be sufficiently volatile to enable formation of an aerosol of the solution or suspension. Additional solvents or aerosolizing agents, such as freons, can be added as desired to increase the volatility of the solution or suspension.

In one embodiment, compositions may contain minor amounts of polymers, surfactants, or other excipients well known to those of the art. In this context, "minor amounts" means no excipients are present that might affect or mediate uptake of the compounds in the lungs and that the excipients that are present are present in amount that do not adversely affect uptake of compounds in the lungs.

Dry lipid powders can be directly dispersed in ethanol because of their hydrophobic character. For lipids stored in organic solvents such as chloroform, the desired quantity of solution is placed in a vial, and the chloroform is evaporated under a stream of nitrogen to form a dry thin film on the surface of a glass vial. The film swells easily when reconstituted with ethanol. To fully disperse the lipid molecules in the organic solvent, the suspension is sonicated. Nonaqueous suspensions of lipids can also be prepared in absolute ethanol using a reusable PARI LC Jet+ nebulizer (PART Respiratory Equipment, Monterey, Calif.).

Dry powder formulations ("DPFs") with large particle size have improved flowability characteristics, such as less aggregation, easier aerosolization, and potentially less phagocytosis. Dry powder aerosols for inhalation therapy are generally produced with mean diameters primarily in the range of less than 5 microns, although a preferred range is between one and ten microns in aerodynamic diameter. Large "carrier" particles (containing no drug) have been co-delivered with therapeutic aerosols to aid in achieving efficient aerosolization among other possible benefits.

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art. The preferred methods of manufacture are by spray drying and freeze drying, which entails using a solution containing the surfactant, spraying to form droplets of the desired size, and removing the solvent.

The particles may be fabricated with the appropriate material, surface roughness, diameter and tap density for localized delivery to selected regions of the respiratory tract such as the deep lung or upper airways. For example, higher density or larger particles may be used for upper airway delivery. Similarly, a mixture of different sized particles, provided with the same or different active agents may be administered to target different regions of the lung in one administration.

6. Topical and Transdermal Formulations

Transdermal formulations may also be prepared. These will typically be gels, ointments, lotions, sprays, or patches, all of which can be prepared using standard technology. Transdermal formulations can include penetration enhancers.

A "gel" is a colloid in which the dispersed phase has combined with the continuous phase to produce a semisolid material, such as jelly.

An "oil" is a composition containing at least 95% wt of a lipophilic substance. Examples of lipophilic substances include but are not limited to naturally occurring and synthetic oils, fats, fatty acids, lecithins, triglycerides and combinations thereof.

A "continuous phase" refers to the liquid in which solids are suspended or droplets of another liquid are dispersed, and is sometimes called the external phase. This also refers to the fluid phase of a colloid within which solid or fluid particles are distributed. If the continuous phase is water (or another hydrophilic solvent), water-soluble or hydrophilic drugs will dissolve in the continuous phase (as opposed to being dispersed). In a multiphase formulation (e.g., an emulsion), the discreet phase is suspended or dispersed in the continuous phase.

An "emulsion" is a composition containing a mixture of non-miscible components homogenously blended together. In particular embodiments, the non-miscible components include a lipophilic component and an aqueous component. An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

"Emollients" are an externally applied agent that softens or soothes skin and are generally known in the art and listed in compendia, such as the "Handbook of Pharmaceutical Excipients", $4^{th}$ Ed., Pharmaceutical Press, 2003. These include, without limitation, almond oil, castor oil, ceratonia extract, cetostearoyl alcohol, cetyl alcohol, cetyl esters wax, cholesterol, cottonseed oil, cyclomethicone, ethylene glycol palmitostearate, glycerin, glycerin monostearate, glyceryl monooleate, isopropyl myristate, isopropyl palmitate, lanolin, lecithin, light mineral oil, medium-chain triglycerides, mineral oil and lanolin alcohols, petrolatum, petrolatum and lanolin alcohols, soybean oil, starch, stearyl alcohol, sunflower oil, xylitol and combinations thereof. In one embodiment, the emollients are ethylhexylstearate and ethylhexyl palmitate.

"Surfactants" are surface-active agents that lower surface tension and thereby increase the emulsifying, foaming, dispersing, spreading and wetting properties of a product. Suitable non-ionic surfactants include emulsifying wax, glyceryl monooleate, polyoxyethylene alkyl ethers, polyoxyethylene castor oil derivatives, polysorbate, sorbitan esters, benzyl alcohol, benzyl benzoate, cyclodextrins, glycerin monostearate, poloxamer, povidone and combinations thereof. In one embodiment, the non-ionic surfactant is stearyl alcohol.

"Emulsifiers" are surface active substances which promote the suspension of one liquid in another and promote the formation of a stable mixture, or emulsion, of oil and water. Common emulsifiers are: metallic soaps, certain animal and vegetable oils, and various polar compounds. Suitable emulsifiers include acacia, anionic emulsifying wax, calcium stearate, carbomers, cetostearyl alcohol, cetyl alcohol, cholesterol, diethanolamine, ethylene glycol palmitostearate, glycerin monostearate, glyceryl monooleate, hydroxpropyl cellulose, hypromellose, lanolin, hydrous, lanolin alcohols, lecithin, medium-chain triglycerides, methylcellulose, mineral oil and lanolin alcohols, monobasic sodium phosphate, monoethanolamine, nonionic emulsifying wax, oleic acid, poloxamer, poloxamers, polyoxyethylene alkyl ethers, polyoxyethylene castor oil derivatives, polyoxyethylene sorbitan fatty acid esters, polyoxyethylene stearates, propylene glycol alginate, self-emulsifying glyceryl monostearate, sodium citrate dehydrate, sodium lauryl sulfate, sorbitan esters, stearic acid, sunflower oil, tragacanth, triethanolamine, xanthan gum and combinations thereof. In one embodiment, the emulsifier is glycerol stearate.

A "lotion" is a low- to medium-viscosity liquid formulation. A lotion can contain finely powdered substances that are in soluble in the dispersion medium through the use of suspending agents and dispersing agents. Alternatively, lotions can have as the dispersed phase liquid substances that are immiscible with the vehicle and are usually dispersed by means of emulsifying agents or other suitable stabilizers. In one embodiment, the lotion is in the form of an emulsion having a viscosity of between 100 and 1000 centistokes. The fluidity of lotions permits rapid and uniform application over a wide surface area. Lotions are typically intended to dry on the skin leaving a thin coat of their medicinal components on the skin's surface.

A "cream" is a viscous liquid or semi-solid emulsion of either the "oil-in-water" or "water-in-oil type". Creams may contain emulsifying agents and/or other stabilizing agents. In one embodiment, the formulation is in the form of a cream having a viscosity of greater than 1000 centistokes, typically in the range of 20,000-50,000 centistokes. Creams are often time preferred over ointments as they are generally easier to spread and easier to remove.

An emulsion is a preparation of one liquid distributed in small globules throughout the body of a second liquid. The dispersed liquid is the discontinuous phase, and the dispersion medium is the continuous phase. When oil is the dispersed liquid and an aqueous solution is the continuous phase, it is known as an oil-in-water emulsion, whereas when water or aqueous solution is the dispersed phase and oil or oleaginous substance is the continuous phase, it is known as a water-in-oil emulsion. The oil phase may consist at least in part of a propellant, such as an HFA propellant. Either or both of the oil phase and the aqueous phase may contain one or more surfactants, emulsifiers, emulsion stabilizers, buffers, and other excipients. Preferred excipients include surfactants, especially non-ionic surfactants; emulsifying agents, especially emulsifying waxes; and liquid non-volatile non-aqueous materials, particularly glycols such as propylene glycol. The oil phase may contain other oily pharmaceutically approved excipients. For example, materials such as hydroxylated castor oil or sesame oil may be used in the oil phase as surfactants or emulsifiers.

A sub-set of emulsions are the self-emulsifying systems. These drug delivery systems are typically capsules (hard shell or soft shell) comprised of the drug dispersed or dissolved in a mixture of surfactant(s) and lipophillic liquids such as oils or other water immiscible liquids. When the capsule is exposed to an aqueous environment and the outer gelatin shell dissolves, contact between the aqueous medium and the capsule contents instantly generates very small emulsion droplets. These typically are in the size range of micelles or nanoparticles. No mixing force is required to generate the emulsion as is typically the case in emulsion formulation processes.

The basic difference between a cream and a lotion is the viscosity, which is dependent on the amount/use of various oils and the percentage of water used to prepare the formulations. Creams are typically thicker than lotions, may have various uses and often one uses more varied oils/butters, depending upon the desired effect upon the skin. In a cream formulation, the water-base percentage is about 60-75% and the oil-base is about 20-30% of the total, with the other percentages being the emulsifier agent, preservatives and additives for a total of 100%.

An "ointment" is a semisolid preparation containing an ointment base and optionally one or more active agents. Examples of suitable ointment bases include hydrocarbon bases (e.g., petrolatum, white petrolatum, yellow ointment, and mineral oil); absorption bases (hydrophilic petrolatum, anhydrous lanolin, lanolin, and cold cream); water-removable bases (e.g., hydrophilic ointment), and water-soluble bases (e.g., polyethylene glycol ointments). Pastes typically differ from ointments in that they contain a larger percentage of solids. Pastes are typically more absorptive and less greasy that ointments prepared with the same components.

A "gel" is a semisolid system containing dispersions of small or large molecules in a liquid vehicle that is rendered semisolid by the action of a thickening agent or polymeric material dissolved or suspended in the liquid vehicle. The liquid may include a lipophilic component, an aqueous component or both. Some emulsions may be gels or otherwise include a gel component. Some gels, however, are not emulsions because they do not contain a homogenized blend of immiscible components.

Suitable gelling agents include, but are not limited to, modified celluloses, such as hydroxypropyl cellulose and hydroxyethyl cellulose; Carbopol homopolymers and copolymers; and combinations thereof. Suitable solvents in the liquid vehicle include, but are not limited to, diglycol monoethyl ether; alklene glycols, such as propylene glycol; dimethyl isosorbide; alcohols, such as isopropyl alcohol and ethanol. The solvents are typically selected for their ability to dissolve the drug. Other additives, which improve the skin feel and/or emolliency of the formulation, may also be incorporated. Examples of such additives include, but are not limited, isopropyl myristate, ethyl acetate, C12-C15 alkyl benzoates, mineral oil, squalane, cyclomethicone, capric/caprylic triglycerides, and combinations thereof.

Foams consist of an emulsion in combination with a gaseous propellant. The gaseous propellant consists primarily of hydrofluoroalkanes (HFAs). Suitable propellants include HFAs such as 1,1,1,2-tetrafluoroethane (HFA 134a) and 1,1,1,2,3,3,3-heptafluoropropane (HFA 227), but mixtures and admixtures of these and other HFAs that are currently approved or may become approved for medical use are suitable. The propellants preferably are not hydrocarbon propellant gases which can produce flammable or explosive vapors during spraying. Furthermore, the compositions preferably contain no volatile alcohols, which can produce flammable or explosive vapors during use.

Buffers are used to control pH of a composition. Preferably, the buffers buffer the composition from a pH of about 4 to a pH of about 7.5, more preferably from a pH of about 4 to a pH of about 7, and most preferably from a pH of about 5 to a pH of about 7. In a preferred embodiment, the buffer is triethanolamine.

Preservatives can be used to prevent the growth of fungi and microorganisms. Suitable antifungal and antimicrobial agents include, but are not limited to, benzoic acid, butylparaben, ethyl paraben, methyl paraben, propylparaben, sodium benzoate, sodium propionate, benzalkonium chloride, benzethonium chloride, benzyl alcohol, cetylpyridinium chloride, chlorobutanol, phenol, phenylethyl alcohol, and thimerosal.

Additional agents that can be added to the formulation include penetration enhancers. In some embodiments, the penetration enhancer increases the solubility of the drug, improves transdermal delivery of the drug across the skin, in particular across the stratum corneum, or a combination thereof. Some penetration enhancers cause dermal irritation, dermal toxicity and dermal allergies. However, the more commonly used ones include urea, (carbonyldiamide), imidurea, N, N-diethylformamide, N-methyl-2-pyrrolidone, 1-dodecal-azacycloheptane-2-one, calcium thioglycate, 2-pyrrolidone, N,N-diethyl-m-toluamide, oleic acid and its ester derivatives, such as methyl, ethyl, propyl, isopropyl, butyl, vinyl and glycerylmonooleate, sorbitan esters, such as sorbitan monolaurate and sorbitan monooleate, other fatty acid esters such as isopropyl laurate, isopropyl myristate, isopropyl palmitate, diisopropyl adipate, propylene glycol monolaurate, propylene glycol monooleatea and non-ionic detergents such as BRIJ® 76 (stearyl poly(10 oxyethylene ether), BRIJ® 78 (stearyl poly(20)oxyethylene ether), BRIJ® 96 (oleyl poly(10)oxyethylene ether), and BRIJ® 721 (stearyl poly (21) oxyethylene ether) (ICI Americas Inc. Corp.). Chemical penetrations and methods of increasing transdermal drug delivery are described in Inayat, et al., *Tropical Journal of Pharmaceutical Research*, 8(2):173-179 (2009) and Fox, et al., *Molecules*, 16:10507-10540 (2011). In some embodiments, the penetration enhancer is, or includes, an alcohol such ethanol, or others disclosed herein or known in the art.

Delivery of drugs by the transdermal route has been known for many years. Advantages of a transdermal drug delivery compared to other types of medication delivery such as oral, intravenous, intramuscular, etc., include avoidance of hepatic first pass metabolism, ability to discontinue administration by removal of the system, the ability to control drug delivery for a longer time than the usual gastrointestinal transit of oral dosage form, and the ability to modify the properties of the biological barrier to absorption.

Controlled release transdermal devices rely for their effect on delivery of a known flux of drug to the skin for a prolonged period of time, generally a day, several days, or a week. Two mechanisms are used to regulate the drug flux: either the drug is contained within a drug reservoir, which is separated from the skin of the wearer by a synthetic membrane, through which the drug diffuses; or the drug is held dissolved or suspended in a polymer matrix, through which the drug diffuses to the skin. Devices incorporating a reservoir will deliver a steady drug flux across the membrane as long as excess undissolved drug remains in the reservoir; matrix or monolithic devices are typically characterized by a falling drug flux with time, as the matrix layers closer to the skin are depleted of drug. Usually, reservoir patches include a porous membrane covering the reservoir of medication which can control release, while heat melting thin layers of medication embedded in the polymer matrix (e.g., the adhesive layer), can control release of drug from matrix or monolithic devices. Accordingly, the active agent can be released from a patch in a controlled fashion without necessarily being in a controlled release formulation.

Patches can include a liner which protects the patch during storage and is removed prior to use; drug or drug solution in direct contact with release liner; adhesive which serves to adhere the components of the patch together along with adhering the patch to the skin; one or more membranes, which can separate other layers, control the release of the drug from the reservoir and multi-layer patches, etc., and backing which protects the patch from the outer environment.

Common types of transdermal patches include, but are not limited to, single-layer drug-in-adhesive patches, wherein the adhesive layer contains the drug and serves to adhere the various layers of the patch together, along with the entire system to the skin, but is also responsible for the releasing of the drug; multi-layer drug-in-adhesive, wherein which is similar to a single-layer drug-in-adhesive patch, but contains multiple layers, for example, a layer for immediate release of the drug and another layer for control release of drug from the reservoir; reservoir patches wherein the drug layer is a liquid compartment containing a drug solution or suspension separated by the adhesive layer; matrix patches, wherein a drug layer of a semisolid matrix containing a drug solution or suspension which is surrounded and partially overlaid by the adhesive layer; and vapor patches, wherein an adhesive layer not only serves to adhere the various layers together but also to release vapor. Methods for making transdermal patches are described in U.S. Pat. Nos. 6,461,644, 6,676, 961, 5,985,311, and 5,948,433.

In a particularly preferred embodiment, THIP or a derivative thereof, is formulated for transdermal delivery and administered using a transdermal patch. In some embodiments, the formulation, the patch, or both are designed for extended release of the THIP or derivative thereof.

Exemplary symptoms, pharmacologic, and physiologic effects are discussed in more detail below.

III. Methods of Treating Secondary Insomnia

Methods of treating secondary insomnia are provided. The methods can include administering to the subject an effective amount of 4,5,6,7-tetrahydroisoxazolo(5,4-c)pyridin-3-ol (THIP) or a derivative thereof to decrease sleep disruption, increase slow wave sleep (SWS) and/or slow wave activity (SWA), normalize sleep architecture, reduce secondary insomnia, increase non-rapid eye movement (NREM) sleep, increase sleep continuity, enhance delta activity within NREM, increase or improve total sleep time (TST), increase or improve sleep efficiency, reduce total time awake (TAA), reduce number of awakenings (NWA), reduce latency to persistent sleep (LPS), reduce wake after sleep onset (WASO), or any combination thereof. In preferred embodiments, REM sleep is not substantially reduced. In some embodiments, the methods are effective to reduce, delay, or prevent one or more other clinical symptoms of a neurodegenerative disease or central nervous system disease or disorder.

A. Treatment Protocol

It has been discovered that THIP and derivatives thereof can be used to treat secondary insomnia. Secondary insomnia is the symptom or side effect of another problem, for example, an emotional, neurological, or other medical or sleep disorder. Accordingly, the subject to be treated typically suffers from both insomnia and an underlying disease, disorder, or condition that is causing the insomnia.

Emotional disorders that can cause insomnia include depression, anxiety, and posttraumatic stress disorder. Conditions that cause chronic pain, such as arthritis and headache disorders; conditions that make it hard to breathe, such as asthma and heart failure; an overactive thyroid; gastrointestinal disorders, such as heartburn; stroke; sleep disorders, such as restless legs syndrome and sleep-related breathing problems; menopause and hot flashes; medication for example asthma medicines, such as theophylline, as well as some allergy and cold medicines, beta blockers, and medicines used to treat heart conditions can also cause secondary insomnia. Use of caffeine and other stimulants, tobacco or other nicotine products, and alcohol or other sedatives can also lead to secondary insomnia.

In a preferred embodiment, the secondary insomnia is caused by a neurological disease or disorder, such as one those described in more detail below.

1. Sleep Architecture

In some embodiments, the subject has or is at risk for developing reduced slow wave sleep, disrupted sleep architecture, or would otherwise benefit from increased slow wave sleep. Therefore, in some embodiments, the compositions are administered in an effective amount to reduce, alleviate, or prevent one or more sleep related symptoms. In preferred embodiments, THIP or derivative thereof is administered to the subject in an effective amount to decrease sleep disruption, increase slow wave sleep (SWS) and/or slow wave activity (SWA), normalize sleep architecture, reduce secondary insomnia, increase non-rapid eye movement (NREM) sleep, increase sleep continuity, enhance delta activity within NREM, increase or improve total sleep time (TST), increase or improve sleep efficiency, reduce total time awake (TAA), reduce number of awakenings (NWA), reduce latency to persistent sleep (LPS), reduce wake after sleep onset (WASO), or any combination thereof. In preferred embodiments, REM sleep is not substantially reduced.

Sleep is an active process generated and modulated by a complex set of neural systems located mainly in the hypothalamus, brainstem, and thalamus. Sleep is altered in many neurological diseases due to mechanisms including lesions of the brain areas that control sleep and wakefulness, lesions or diseases that produce pain, reduced mobility, and treatments. Excessive daytime sleepiness (EDS), sleep fragmentation, insomnia, sleep-disordered breathing (SDB), nocturnal behavioral phenomena such as rapid eye movement (REM) sleep behavior disorder or nocturnal seizures, restless legs syndrome, and periodic leg movement syndrome (PLMS) are common symptoms and findings in neurological disorders (Jennum, et al., "CHAPTER 39: Sleep disorders in neurodegenerative disorders and stroke", *European Handbook of Neurological Management*, Volume 1, 2nd Edition (Ed. Gilhus, et al.) Blackwell Publishing Ltd. 2011). In some cases, sleep disorders precede and influence the disease course in neurological diseases, particularly those involving daytime functioning, quality of life, morbidity, and mortality.

Evidence is also emerging that subjects with HD can suffer from abnormalities in both sleep and in the control of daily or 'circadian' rhythms (Morton, "HDBuzz Special Feature: Huntington's disease and sleep" HDbuzz.net/115, (ed., Wild), Feb. 6, 2013). Therefore, sleep and circadian dysfunction are symptoms of HD. Other sleep-related symptoms in patients with Huntington's disease in the diminishment of involuntary movements tend to diminish during sleep, sleep disturbances, including disturbed sleep pattern with an increased sleep onset latency, reduced sleep efficiency, frequent nocturnal awakenings, and more time spent awake with less slow wave sleep. These abnormalities can correlate in part with the duration of illness, severity of clinical symptoms, and degree of atrophy of the caudate nucleus. The sleep phenotype of Huntington's disease may also include insomnia, advanced sleep phase, periodic leg movements, REM sleep behavior disorder (RBD), and reduced REM sleep. Reduced REM sleep may precede chorea, and mutant huntingtin may exert an effect on REM sleep and motor control during sleep.

Sleep-wake problems are also frequent, although often unrecognized, complications of amyotrophic lateral sclerosis (ALS). Sleep disorders such as insomnia, sleep-disordered breathing and restless legs syndrome have all been reported in patients with ALS, despite the limited number of studies and the small populations investigated so far (Lo Coco, et al., *Neurodegenerative Disease Management*, 2(3): 315-324 (2012)). The prognosis in ALS is closely related to respiratory muscle strength, and sudden nocturnal death often occurs during sleep. Respiratory indices such as low nocturnal oxygen saturation are associated with a poorer prognosis. Patients with diaphragmatic involvement may have significantly reduced REM sleep. Patients with dementias often present circadian disturbances which have been treated with melatonin and light therapy.

Sleep and circadian dysfunction may be caused by other symptoms of the neurodegenerative disease, or may be caused by factors that are independent of the disease. Sleep and circadian dysfunction can be caused by personal habits, lifestyle or environment, for example, staying up too late, getting up too early, taking drugs that interfere with sleep, and/or over-stimulation due to late-night activities such as work, television, etc. Sleep and circadian disturbance in neurodegenerative disease patients are likely to contribute to disease symptoms that are worsened by sleep deprivation, such as irritability and anxiety, and may precede and influence the disease course involving daytime functioning, quality of life, morbidity, and mortality. For example, sleep disturbances have been reported to gradually worsen with disease progression in ALS, indicating a relationship between the severity of disease and the neurodegenerative process. Furthermore, subjects with a neurodegenerative disease may not have the same neurological reserves to handle sleep deprivation that healthy subjects rely upon.

Poor sleep can also be a consequence of several disturbances such as anxiety, depression, pain, choking, sialorrhea, fasciculations, cramps, nocturia and the inability to get comfortable and move freely in bed. Sleep disorders may have many reflections on patients including excessive daytime somnolence, fatigue, impaired cognition, reduced quality of life and survival (Lo Coco, et al., *Neurodegenerative Disease Management*, 2(3):315-324 (2012)).

Circadian rhythms and sleep are two different processes, although the terms are often used interchangeably. Circadian rhythms are biological processes that change roughly every 24 hours. They are orchestrated by a small part of the brain known as the suprachiasmatic nucleus or SCN, which regulates the body's activities including when to get up and when to go to bed. Sleep is a circadian behavior, but is just one of many circadian behaviors that are influenced by the SCN. Others include heart rate, hormone secretion, blood pressure and body temperature.

During the night, sleep follows a predictable pattern, moving back and forth between deep restorative sleep (deep sleep) and more alert stages (collective referred to as Non- REM or NREM) and dreaming (REM sleep). Specifically, the sleep cycle includes stages W (wakefulness), N1 (NREM 1), N2 (NREM 2), N3 (NREM3), and R (REM). Sleep stages can be identified by monitoring a subject's brain electrical activity (e.g., brain waves). The criteria for each stage, and methods for determining the stage of a sleeping subject, and profiling a subject's sleep architecture are described in Iber, et al., "The AASM Manual for the Scoring of Sleep and Associated Events, American Academy of Sleep Medicine", pg. 1-57 (2007), which is specifically incorporated by reference herein in its entirety.

Together, the stages of REM and non-REM sleep form a complete sleep cycle. Each cycle typically lasts about 90 minutes and repeats four to six times over the course of a typical night's sleep. A normal adult spends approximately 50% of total sleep time in Stage 2 sleep, 20% in REM sleep, and 30% in the remaining stages, including deep sleep. For example, a typical first sleep cycle, N1, is characterized by a low-voltage, mixed-frequency pattern, and may last for about 1 to about 10 minutes. The second stage, N2, comes next is characterized by sleep spindles and/or K complexes in the EEG recording. N2 generally lasts about 10 to about 25 minutes. As N2 sleep progresses, there is a gradual appearance of the high-voltage, slow-wave activity characteristic of N3, the third stage of NREM sleep. This stage, which generally lasts about 20 to about 40 minutes, is referred to as "slow-wave," "delta," or "deep" sleep. Following the N3 stage of sleep, a series of body movements usually signals an "ascent" to lighter NREM sleep stages. Typically, a 5 to 10 minute period of N2 precedes the initial REM sleep episode. REM sleep episodes, the first of which may last only one to five minutes, generally become longer through the night. During a typical night, N3 sleep occupies less time in the second cycle than the first and may disappear altogether from later cycles. The average length of the first NREM-REM sleep cycle is between 70 and 100 minutes; the average length of the second and later cycles is about 90 to 120 minutes. REM sleep makes up about 20 to 25 percent of total sleep in typical healthy adults ("Natural Patterns of Sleep" healthysleep.med.harvard.edu/healthy/science/what/sleep-patterns-rem-nrem, A resource from the Division of Sleep Medicine at Harvard Medical School (2007)).

The duration of the stages of the sleep cycle alone, or in combination with the cycling of the stages can be referred to as a subject's sleep architecture. In some embodiments, neurodegenerative disease subjects have disrupted sleep architecture, for example, an alteration in the duration of one or more sleep cycles, an alternation in the duration or number of sleep cycles, or any combination thereof compared to a control or reference value. A control or reference value in this case can be, for example, an average, normal duration for the stage, or average normal duration or number of cycles in subject or subjects that do not suffer from disrupted or disturbed sleep architecture (e.g., a healthy subject).

Therefore, in some embodiments, THIP or a derivative thereof is administered to a subject in an effective amount to normalize a subject's sleep architecture, for example, by bringing one or more aspects of the subject's sleep architecture into closer alignment with that of a normal subject.

Slow-wave sleep (SWS), often referred to as deep sleep, consists of N3, non-rapid eye movement sleep. The 1968 categorization of the combined Sleep Stages 3-4 was reclassified in 2007 as Stage N3. An epoch (30 seconds of sleep) which consists of 20% or more of slow wave (delta) sleep, is now considered to be stage 3 (Gazzaniga, *Just the Facts 101, e-Study Guide for: Psychological Science*, Content Technologies Inc., 2014). Slow-wave sleep is believed to be important to consolidate new memories, and sleep deprivation studies with humans indicate that among other things, an important function of slow-wave sleep may be to allow the brain to recover from its daily activities.

Rapid eye movement (REM) sleep is a stage of sleep characterized by the rapid and random movement of the eyes and can be classified into two categories: tonic and phasic. Criteria for REM sleep includes rapid eye movement, low muscle tone and a rapid, low-voltage EEG—features which can be identified by polysomnogram. REM sleep typically occupies 20-25% of total sleep, about 90-120 minutes of a night's sleep.

In some embodiments THIP or a derivative thereof is administered to a subject in an effective amount to increase the length of one or more N3 stages during a subject's sleep, increase the number of N3 stages during a subject's sleep, or a combination thereof. In some embodiments, the compositions increase slow wave sleep by at least 15 minutes, at least 30 minutes, at least 45 minutes, at least 60 minutes, at least 75 minutes, at least 90 minutes, or at least 120 minutes over the course of the sleeping period (e.g., overnight). In some embodiments the compositions double or more the amount of slow wave sleep in the subject.

2. Dosage and Administration

The disclosed methods of treating secondary insomnia typically include administering to a subject in need thereof an effective amount of THIP or a derivative thereof, preferably is a pharmaceutically acceptable composition such as those discussed in more detail above.

The effective amount or therapeutically effective amount is typically a dosage sufficient to decrease sleep disruption, increase slow wave sleep (SWS) and/or slow wave activity (SWA), normalize sleep architecture, reduce secondary insomnia, increase non-rapid eye movement (NREM) sleep, increase sleep continuity, enhance delta activity within NREM, increase or improve total sleep time (TST), increase or improve sleep efficiency, reduce total time awake (TAA), reduce number of awakenings (NWA), reduce latency to persistent sleep (LPS), reduce wake after sleep onset (WASO), or any combination thereof. In preferred embodiments, REM sleep is not substantially reduced.

In some embodiment the method reduces or prevents one or more neuropsychiatric morbidities in a subject with a neurodegenerative disease or disorder. Therefore, the amount can be effective to treat or prevent one or more symptoms of a neurodegenerative disease or central nervous system disorder, or to otherwise provide a desired pharmacologic and/or physiologic effect.

The precise dosage will vary according to a variety of factors such as subject-dependent variables (e.g., age, immune system health, clinical symptoms etc.). Exemplary dosages, symptoms, pharmacologic, and physiologic effects are discussed in more detail below.

Studies of the effect of gaboxadol in improving sleep in subjects are discussed and reviewed in Walsh, et al., *Journal of Clinical Sleep Medicine*, 5(2):527-532 (2009) and Deacon, et al., *Sleep*, 30(3):281-287 (2007). For example, 15 mg of gaboxadol resulted in significantly more stage 4 sleep and SWS (but not stage 3) compared with the placebo group (both $p<0.001$) in subjects under sleep-restriction (a mean of 21.8 minutes more SWS was seen with gaboxadol compared to placebo over four sleep-restriction nights), Walsh, et al., *Journal of Clinical Sleep Medicine*, 5(2):527-532 (2009). Gaboxadol also resulted in small but significant reductions in stage 1 sleep, REM sleep, and shifts to wake or stage 1 sleep relative to placebo.

In another dose-response study, 5, 10, or 15 mg gaboxadol was administered to 109 healthy subjects in whom habitual sleep time was advanced by 4 hours to produce transient sleep disruption (Walsh, et al., *Sleep,* 30:593-602 (2007)). The study results show that gaboxadol produced a dose-related increase of approximately 5 to 22 minutes in SWS compared with placebo. TST was significantly increased by approximately 30 minutes (p<0.001) and WASO was reduced by approximately 17-20 minutes (p<0.05) compared to placebo at all dosages. Subjective measures of sleep quality also improved with gaboxadol relative to placebo.

A dose-related study of 40 primary insomnia subjects administered 10 and 20 mg of gaboxadol also reported an increase in SWS compared with placebo (10 mg: p<0.01; 20 mg: p<0.001) (Lundahl, et al., *Psychopharmacology (Berl),* 195:139-46 (2007). Gaboxadol at dosage of 20 mg significantly reduced WASO (p<0.01), and both doses of gaboxadol significantly reduced NASO (p<0.001). Gaboxadol at a dosage of 20 mg also significantly increased TST (p<0.05).

In another study of the effect of gaboxadol on 26 patients with primary insomnia, 15 mg was shown to enhance SWS in a study without significantly affecting stage 1, stage 2, or REM sleep (Deacon, et al., *Sleep,* 30(3):281-287 (2007)). Gaboxadol at dosages 5 mg and 15 mg significantly improved TST (p<0.05). The results also indicate that WASO improved, however, statistical significance was only achieved with the 5 mg dose. A gaboxadol dosage of 15 mg also significantly reduced latency to persistent sleep (p<0.05).

Furthermore, in pre-clinical studies and in studies in healthy young and elderly individuals, gaboxadol was found to increase NREM sleep, sleep continuity, enhances delta activity within NREM sleep, and increase SWS/SWA without suppressing REM sleep (Lancel, et al., *Neuroreport,* 7:2241-5 (1996), Lancel, et al., *Sleep,* 20:1099-104 (1997), Faulhaber, et al., *Psychopharmacology (Berl),* 130:285-91 (1997), Lancel, *Sleep;* 22:33-42 (1999), Lancel, et al., *Am J Physiol Endocrinol Metab,* 281:E130-7 (2001), Mathias, et al., *Psychopharmacology (Berl),* 157:299-304 (2001), Mathias, et al., *Neuropsychopharmacology,* 30:833-41 (2005)).

In preferred embodiments, THIP or derivative thereof is administered to a subject in an effective amount to increase slow wave sleep in the subject.

Particularly preferred embodiments include formulations for extended release. For example, the formulation can be suitable for administration once daily or less. In some embodiments, the composition is only administered to the subject once every 24-48 hours. In some embodiments, THIP or a derivative thereof is administered at night before sleep. In other embodiments, THIP or a derivative thereof is administered in morning, or at least several hours before sleep.

The timing of the administration of the composition will depend on the formulation and/or route of administration used. In some embodiments, administration of the composition will be given as a long-term treatment regimen whereby pharmacokinetic steady state conditions will be reached. Medication for peroral or parenteral administration may also be given in immediate relation to a particular sleeping period, for instance 10 minutes to 3 hours prior to the onset of sleep. Thus, the composition can be administered in immediate relation to a particular sleeping period, for example, from 5 minutes to 5 hours prior to onset of sleep, 10 minutes to 3 hours prior to the onset of sleep.

A preferred route of administration is transdermal, for example, a transdermal patch or gel that is contacted with the skin of the subject. In a particular embodiment, the transdermal formulation is administered to a subject prior to the subject going to sleep (e.g., at night) using a transdermal patch. In another particular embodiment, the transdermal formulation is administered to a subject in the morning using a transdermal patch. As discussed in more detail below, in some methods a subject with a neurodegenerative disease or central nervous system disorder is transdermally administered an amount of THIP or a derivative thereof effective to decrease sleep disruption or increase slow wave sleep in the subject.

In general, by way of example only, dosage forms useful in the disclosed methods can include doses in the range of 0.1 to 1,000 mg, 1 to 200 mg, 5 to 175 mg, 7.5 to 150 mg, or 10 to 125 mg, or 12.5 to 150 mg, or 15 to 125 mg, or 17.5 to 100 mg, or 20 to 75 mg, or 22.5 to 60 mg, or 25 to 50 mg, with doses of 1 mg, 5 mg, 10 mg, 15 mg, 20 mg, 25 mg, 30 mg, 35 mg, 40 mg, 45 mg, 50 mg, 55 mg, 60 mg, 75 mg, and 100 mg being specific examples of preferred doses. Typically, such dosages are administered once, twice, or three times daily, or every other day to a human.

A typical oral dose form preferably includes from about 2.5 mg to about 30 mg THIP. Preferably, the THIP is in a crystalline form. Further embodiments of the medicament comprises an effective amount of THIP from 2.5 mg to 20 mg, such as 2.5 mg to 4 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg, e.g. 2.5 mg, 5 mg, 7.5 mg, 10 mg, 12.5 mg, 15 mg, 17.5 mg, or 20 mg. A typical embodiment is about 5 mg to about 20 mg of crystalline THIP, such as the hydrochloride of THIP. Typically, such dosages are administered once, twice, or three times daily, or every other day to a human. In some embodiments, the total amount administered to a subject in 24 hour period is 1 mg to 50 mg. In some embodiments, the subject is started at a low dose and the dosage is escalated in the drug is well tolerated in the subject.

When given orally in healthy subjects, gaboxadol is rapidly absorbed (tmax of 30-60 min) and eliminated (t½ of 1.5 h) (Deacon, et al., *Sleep,* 30(3):281-287 (2007)). More than 95% of the dose is excreted in the urine, mostly unchanged, with a glucoronide conjugate being the only metabolite formed in significant amounts.

In some embodiments, the effect of the composition on a subject is compared to a control. For example, the effect of the composition on a particular symptom, pharmacologic, or physiologic indicator can be compared to an untreated subject, or the condition of the subject prior to treatment. In some embodiments, the symptom, pharmacologic, or physiologic indicator is measured in a subject prior to treatment, and again one or more times after treatment is initiated. In some embodiments, the control is a reference level, or average determined based on measuring the symptom, pharmacologic, or physiologic indicator in one or more subjects that do not have the disease or condition to be treated (e.g., healthy subjects). In some embodiments, the effect of the treatment is compared to a conventional treatment that is known the art, such as one of those discussed herein.

3. Intravenous Delivery

In some embodiments, the composition is administered by intravenous injection or infusion. When administered orally, transport of gaboxadol from the intestine into the portal circulation takes place via the transporter PAT1. Because the amino acid substrates of the PAT1 transporter, including but not limited to, proline, tryptophan, alanine, and glycine, are present in food, their presence during oral administration can influence absorption of the gaboxadol. More specifically, PAT1 inhibitors such as L-tryptophan can decrease the absorption rate constant, $k_a$, and $C_{max}$, and increase $T_{max}$ of gaboxadol (see, for example, Larsen, et al., *Br. J. Pharmacol.*, 157(8):1380-1389 (2009) and WO 2009/056146). Therefore, it is believed that intravenous administration can improve control of plasma levels (and brain levels) over oral administration due to significant variability of gaboxadol uptake via the oral route. Furthermore, high peak concentrations of gaboxadol in predisposed individuals leads to hallucinations and has resulted in discontinuation of the drug's administration to some subjects. Intravenous delivery provides the ability to titrate dose which ensures that high peak $C_{max}$ is not observed, and helps avoid this potential adverse event.

In some embodiments, the use of intravenous administration allows for the composition to be delivered in a lower dosage than, for example, when it is delivered orally. A preferred rate for IV delivery is 0.001 mg/kg per hour to 1 mg/kg per hour. The treatment can be administered for the course of minutes, hours, or days. Dosages, including totally daily dosages, are discussed above. In particular embodiments, a single treatment includes intravenously administering to a subject in need thereof a total of between about 0.001 mg and about 30 mg of THIP or derivative thereof. In some embodiments, the administration is repeated at least once with an interval of about 3 to about 5 hours. In some embodiments, the administration is repeated at least six times in a period of twenty-four hours. In various embodiments, the administration is repeated three to eight times (e.g., three times, four times, five times, six times, seven times, or eight times) in a period of twenty-four hours and between about 0.001 mg and about 30 mg of THIP or derivative thereof is delivered over the twenty-four hour period. Dosage regimens are also discussed above. For example, in some embodiments, a single treatment can be repeated 1, 2, 3, 4, 5, 6, 7, or more days, weeks, or months apart. Intravenous administration increases the ease with which side effects associated with dosage escalation can be monitored, improves the ability to control plasma concentrations, and includes the ability to titrate dosage. Accordingly, in some embodiments, the intravenous dosage regimen includes escalation of the dosage from 0.001 mg to about 30 mg of THIP or derivative thereof in a twenty-four hour period, until the dosage is effective to treat the subject, and preferably without inducing undesirable side effects. Intravenous protocols can also be adapted from those known in the art. See, for example, U.S. Published Application 2009/0143474.

B. Conditions, Symptoms, Subjects, and Diseases to be Treated

The disclosed compositions are typically administered to subjects with a neurodegenerative disease or disorder or central nervous system disorder, particularly those leading to secondary insomnia in the subject. Neurodegeneration refers to the progressive loss of structure or function of neurons, including death of neurons. Exemplary diseases and disorders are provided below. In some embodiments, the compositions are administered to subjects that do not have a neurodegenerative disease or disorder.

Neurodegeneration, and diseases and disorders thereof, can be caused by a genetic mutation or mutations; protein misfolding; intracellular mechanisms such as dysregulated protein degradation pathways, membrane damage, mitochondrial dysfunction, or defects in axonal transport; defects in programmed cell death mechanisms including apoptosis, autophagy, cytoplasmic cell death; and combinations thereof. More specific mechanisms common to neurodegenerative disorders include, for example, oxidative stress, mitochondrial dysfunction, excitotoxicity, inflammatory changes, iron accumulation, and/or protein aggregation.

1. Symptoms

In some embodiments, the disclosed compositions are administered to a subject in need thereof in an effective amount to reduce or prevent one or more molecular or clinical symptoms of a neurodegenerative disease, or one or more mechanisms that cause neurodegeneration. Symptoms of neurodegenerative diseases are known in the art and vary from disease to disease. In some embodiments, the disease exhibits or is characterized by one or any combination of the following symptoms or diseases: stress, anxiety, seasonal depression, insomnia and tiredness, schizophrenia, panic attacks, melancholy, dysfunction in the regulation of appetite, insomnia, psychotic problems, epilepsy, senile dementia, various disorders resulting from normal or pathological aging, migraine, memory loss, disorders of cerebral circulation, cardiovascular pathologies, pathologies of the digestive system, fatigue due to appetite disorders, obesity, pain, psychotic disorders, diabetes, senile dementia, or sexual dysfunction. In some embodiments, the subject does not exhibit one or more of the preceding symptoms.

In some embodiments, the subject has been medically diagnosed as having a neurodegenerative disease or a condition in need of neuroprotection by exhibiting clinical (e.g., physical) symptoms of the disease. As discussed above, in some patients the appearance of sleep-related disorder precedes a clinical diagnosis of a disease. Therefore, in some embodiments, the compounds or compositions disclosed herein are administered prior to a clinical diagnosis of a disease or condition. In some embodiments, a genetic test indicates that the subject has one or more genetic mutations associated with a neurodegenerative disease or central nervous system disorder.

Neurodegenerative diseases are typically more common in aged individuals. Therefore in some embodiments, the subject is greater the 40, 45, 50, 55, 60, 65, 70, 75, 80, 85, 90, 95, 100 years in age.

2. Diseases to be Treated

The methods disclosed herein can be used to treat subjects with a neurodegenerative disease or disorder. Exemplary neurodegenerative diseases include, but are not limited to, Parkinson's Disease (PD) and PD-related disorders, Huntington's Disease (HD), Amyotrophic Lateral Sclerosis (ALS), Alzheimer's Disease (AD) and other dementias, Prion Diseases such as Creutzfeldt-Jakob Disease, Corticobasal Degeneration, Frontotemporal Dementia, HIV-Related Cognitive Impairment, Mild Cognitive Impairment, Motor Neuron Diseases (MND), Spinocerebellar Ataxia (SCA), Spinal Muscular Atrophy (SMA), Friedreich's Ataxia, Lewy Body Disease, Alpers' Disease, Batten Disease, Cerebro-Oculo-Facio-Skeletal Syndrome, Corticobasal Degeneration, Gerstmann-Straussler-Scheinker Disease, Kuru, Leigh's Disease, Monomelic Amyotrophy, Multiple System Atrophy, Multiple System Atrophy With Orthostatic Hypotension (Shy-Drager Syndrome), Multiple Sclerosis (MS), Neurodegeneration with Brain Iron Accumulation, Opsoclonus Myoclonus, Posterior Cortical Atrophy, Primary Progressive Aphasia, Progressive Supranuclear Palsy, Vascular Dementia, Progressive Multifocal Leukoencephalopathy, Dementia with Lewy Bodies, Lacunar syndromes, Hydrocephalus, Wernicke-Korsakoff's syndrome, post-encephalitic dementia, cancer and chemotherapy-associated cognitive impairment and dementia, and depression-induced dementia and pseudodementia.

In some embodiments, the subject has a central nervous system disorder or is in need of neuroprotection. Exemplary conditions and/or subjects include, but are not limited to, subjects having had, subjects with, or subjects likely to develop or suffer from a stroke, a traumatic brain injury, a spinal cord injury, Post Traumatic Stress syndrome, or a combination thereof.

a. Huntington's Disease

The methods disclosed herein can be used to treat subjects with Huntington's disease. Huntington's disease (HD) is a neurodegenerative genetic disorder that affects muscle coordination and leads to cognitive decline and psychiatric problems. The chronic pathology in HD leads to numerous associated troubles including cognitive dysfunctions, more specifically dysfunction in thought and mental representations, changes in reasoning, in judgment. HD is caused by an autosomal dominant mutation in either of an individual's two copies of the Huntingtin (HTT) gene. Part of this gene is a repeated section called a trinucleotide repeat, which varies in length between individuals and may change length between generations. If the repeat is present in a healthy gene, a dynamic mutation may increase the repeat count and result in a defective gene. When the length of this repeated section reaches a certain threshold, it produces an altered form of the protein, called mutant Huntingtin protein (mHtt). The differing functions of these proteins are the cause of pathological changes which in turn cause the disease symptoms. The Huntington's disease mutation is genetically dominant and almost fully penetrant. Mutation of either of a person's HTT genes can cause the disease. Physical symptoms of Huntington's disease can begin at any age from infancy to old age, but usually begin between 35 and 44 years of age (Walker, et al., *Lancet,* 369(9557):218-28 (2007)).

In some embodiments, the subject exhibits one or more of the HD clinical symptoms, one or more HD molecular symptoms, or a combination thereof, such as those discussed herein and elsewhere. Clinical symptoms of HD are known in the art and include behavioral disturbances including, but not limited to, hallucinations, irritability, moodiness, restlessness, fidgeting, paranoia, psychosis, suicidal thoughts, and suicide attempts; abnormal and/or unusual movements including, but not limited to, chorea, facial movements such as grimaces, head turning to shift eye position, quick, sudden, sometimes wild jerking movements of the arms, legs, face, and other body parts, slow, uncontrolled movements, unsteady gait, small unintentionally initiated or uncompleted motions, and lack of coordination; cognitive impairment and/or dementia-related symptoms including, but not limited to, disorientation and/or confusion, loss of judgment, loss of memory, personality changes, and speech changes; and other symptoms including anxiety, stress, tension, difficulty swallowing, speech impairment, rigidity, slow movements, tremor, malnutrition, and weight loss. Neuropsychiatric features are a core component of the disease.

Mutant Huntingtin is expressed throughout the body and associated with abnormalities in peripheral tissues that are directly caused by such expression outside the brain. These abnormalities include muscle atrophy, cardiac failure, impaired glucose tolerance, weight loss, osteoporosis and testicular atrophy.

A number of studies have examined the prevalence of the myriad of symptoms in subjects with Huntington's disease. Shiwach, *Acta Psychiatr Scand,* 90(4):241-6 (1994) reports the results of a retrospective study of 110 patients with Huntington disease in 30 families. The study found the minimal lifetime prevalence of depression to be 39%. The frequency of symptomatic schizophrenia was 9%, and significant personality change was found in 72% of the sample. The age at onset was highly variable. Some showed signs in the first decade and some not until over 60 years of age.

Rosenberg, et al., *J Med Genet.,* 32(8):600-4 (1995) describes a double-blind study on 33 persons at risk for HD who had applied for genetic testing. Significantly inferior cognitive functioning was disclosed in gene carriers by a battery of neuropsychologic tests covering attentional, visuospatial, learning, memory, and planning functions. Primarily, attentional, learning, and planning functions were affected.

Bamford, et al., *Neurology,* 45(10):1867-73 (1995) reports a prospective analysis of neuropsychologic performance and CT scans of 60 individuals with Huntington's disease. The study found that psychomotor skills showed the most significant consistent decline among cognitive functions assessed.

Marshall, et al., *Arch Neurol.,* 64(1):116-21 (2007) reports a study comparing psychiatric manifestations among 29 HD mutation carriers with no clinical symptoms, 20 HD mutation carriers with mild motor symptoms, 34 manifesting HD patients, and 171 nonmutation controls. The mild motor symptoms group and the manifesting HD group showed significantly higher scores for obsessive-compulsive behavior, interpersonal sensitivity, anxiety, paranoia, and psychoticism compared to the nonmutation control group. The mutation carriers without symptoms had higher scores for anxiety, paranoid ideation, and psychoticism compared to the nonmutation control group. The results indicated that individuals in the preclinical stage of HD exhibit specific psychiatric symptoms, and that additional symptoms may manifest later in the disease course. Suicidal ideation is a frequent finding in Huntington disease and physicians should be aware of increased suicide risk both in asymptomatic at-risk patients and symptomatic patients (Walker, et al., *Lancet,* 369(9557):218-28 (2007)).

The mechanisms underlying HD are explored in Wang, et al., *Journal of Neuroscience,* 31(41):14496-14507 (2011), which is discussed in more detail below. The study shows that mutant huntingtin (htt)-mediated toxicity in cells, mice, and humans is associated with loss of the type 1 melatonin receptor (MT1). High levels of MT1 receptor were found in mitochondria from the brains of wild-type mice but much less in brains from HD mice, melatonin inhibited mutant htt-induced caspase activation and preserved MT1 receptor expression. Therefore, in some embodiments, the compounds and compositions disclosed herein are administered to a subject with HD in an effective amount to treat one or more molecular symptoms of HD, for example, to reduce, delay or inhibit mutant htt-induced caspase activation; to reduce or prevent loss of MT1 receptor expression, particularly in the mitochondria of cell of the subject; or a combination thereof.

In some embodiments, the subject exhibits one or more symptoms discussed herein, but does not exhibit all of the symptoms. Therefore, in some embodiments, the subject does not have one or more of the symptoms disclosed herein or elsewhere.

In some embodiments, the subject has been medically diagnosed as having HD by exhibiting clinical (e.g., physical) symptoms of the disease. Excessive unintentional movements of any part of the body are often the first clinical symptoms. If these are abrupt and have random timing and distribution, they suggest a diagnosis of HD. Cognitive or psychiatric symptoms are rarely the first diagnosed and are most typically only recognized in hindsight or when they develop further. Disease progression can be measured using the unified Huntington's disease rating scale which provides an overall rating system based on motor, behavioral, cognitive, and functional assessments (Huntington Study Group, *Movement Disorders*, 11(2): 136-142 (1996)).

Medical imaging, such as computerized tomography (CT) and magnetic resonance imaging (MRI), and functional neuroimaging techniques, such as fMRI and PET, can supplement analysis of physical symptoms but are typically not diagnostic alone.

Genetic testing can be used to confirm a physical diagnosis if there is no family history of HD. Even before the onset of symptoms, genetic testing can confirm if an individual or embryo carries an expanded copy of the trinucleotide repeat in the HTT gene that causes the disease. The U.S. government sponsored genetic disease compendium, the Online Mendelian Inheritance in Man (OMIM) database, gives HD a phenotype number #143100. The gene/locus is huntingtin (HTT), and is located on Chromosome 4p16.3 with the Gene/Locus MIM number of 613004. Assignment of the 143100 number to the OMIM entry is because Huntington disease (HD) is a monogenetic disorder caused by an expanded trinucleotide repeat (CAG)n, encoding glutamine, in the gene encoding huntingtin (HTT; 613004) on chromosome 4p16.3. The genetic test for HD consists of a blood test which counts the numbers of CAG repeats in each of the HTT alleles.

Cutoffs for genetic testing are given as follows according to De Die-Smulders, et al., *Human Reproduction Update*, 19(3):304-315 (2013).

40 or more CAG repeats: full penetrance allele (FPA). A "positive test" or "positive result" generally refers to this case. A person who tests positive for the disease will develop HD sometime within their lifetime, provided he or she lives long enough for the disease to appear.

36 to 39 repeats: incomplete or reduced penetrance allele (RPA). It may cause symptoms, usually later in the adult life. There is a maximum risk of 60% that a person with an RPA will be symptomatic at the age of 65 years, and a 70% risk of being symptomatic at the age of 75 years.

27 to 35 repeats: intermediate allele (IA), or large normal allele. It is not associated with symptomatic disease in the tested individual, but may expand upon further inheritance to give symptoms in offspring.

26 or less repeats: Not associated with HD.

A positive result is considered different than a clinical diagnosis, since it may be obtained decades before the symptoms begin. The test can tell a person who originally had a 50 percent chance of inheriting the disease if their risk goes up to 100 percent or is eliminated.

Elsewhere, the range of repeat numbers for normal individual is 9 to 36, and 37 or greater in HD individuals (Duyao et al., *Nat Genet.*, 4(4):387-92 (1993)).

Therefore, in some embodiments, the subject has a "positive result", or is determined to have incomplete or reduced penetrance allele (RPA), or is determined to have intermediate allele (IA), or large normal allele by genetic testing, but does not exhibit any of the clinical symptoms, or the clinical symptoms are too mild for an affirmative medical diagnosis. In a particular embodiment, the subject has a "positive result" but does not exhibit any of the clinical symptoms, or the clinical symptoms are too mild for an affirmative medical diagnosis. Accordingly, in some embodiments, the compounds or compositions disclosed herein are administered prior to a clinical diagnosis of HD.

b. Parkinson's Disease

In a particular embodiment, the disclosed compositions are used to treat a subject with Parkinson's disease or suffering from parkinsonism or parkinson's syndrome. PD is a degenerative disorder of the central nervous system. In some embodiments, the subject exhibits one or more of the PD clinical symptoms, one or more PD molecular symptoms, or a combination thereof, such as those discussed herein and elsewhere. Symptoms of PD are well known in the art and reviewed in Jankovic, et al., J. Neurol. *Neurosurg. Psychiatr.*, 79(4): 368-76 (2007). The motor symptoms of Parkinson's disease result from the death of dopamine-generating cells in the substantia nigra, a region of the midbrain. The cause of the cell death remains unknown. Early in the course of the disease, the most obvious symptoms are movement-related and include, but are not limited to, shaking, rigidity, slowness of movement and difficulty with walking and gait. In particular, four motor symptoms considered hallmarks of PD are tremor, rigidity, slowness of movement, and postural instability. The main motor symptoms are collectively called parkinsonism, or a "parkinsonian syndrome".

Later, thinking and behavioral problems may arise and can range from mild to severe, with dementia commonly occurring in the advanced stages of the disease, whereas depression is the most common psychiatric symptom. Other common neuropsychiatric disturbances include disorders of speech, cognition, mood, behavior, and thought. Cognitive disturbances, which can occur in the initial stages of the disease and sometimes prior to diagnosis, include executive dysfunction, which can include problems with planning, cognitive flexibility, abstract thinking, rule acquisition, initiating appropriate actions and inhibiting inappropriate actions, and selecting relevant sensory information; fluctuations in attention and slowed cognitive speed; and memory loss.

Other symptoms include sensory, sleep and emotional problems. In fact, disturbances of sleep and wake are among the most common and disabling non-motor manifestations of PD, affecting as many as 90% of patients (Videnovic, et al., *JAMA Neurol.* doi:10.1001/jamaneurol.2013.6239, published online Feb. 24, (2014)).

A physician's diagnosis of PD typically comes from a combination of medical history and neurological examination. Brain scans of people with PD typically look normal, but can be used to rule out disorders that could give rise to similar symptoms. Although no lab test exists for PD, medical organizations have created diagnostic criteria to facilitate and standardize the diagnostic process. See, for example, the UK Parkinson's Disease Society Brain Bank, the U.S. National Institute of Neurological Disorders and Stroke, and the PD Society Brain Bank which all provide criteria for diagnosing PD.

Parkinson's disease is more common in older people, with most cases occurring after the age of 50. There is no cure for PD, and the disease is most typically managed using one or a combination of levodopa (usually combined with a dopa decarboxylase inhibitor or COMT inhibitor), dopamine agonists and MAO-B inhibitors. Other common agents include amantadine and anticholinergics for treating motor symptoms, clozapine for treating psychosis, cholinesterase inhibitors for treating dementia, and modafinil for treating daytime sleepiness. Surgery and deep brain stimulation can be used, most typically when drugs are no longer effective. Gene therapies, stem cell transplants, neuroprotective agents, are also being developed as treatment options for PD.

In some embodiments, the subject exhibits one or more of the PD clinical symptoms, one or more ALS molecular symptoms, or a combination thereof, such as those discussed herein and elsewhere. In some embodiments, the subject exhibits one or more symptoms discussed herein, but does not exhibit all of the symptoms. Therefore, in some embodiments, the subject does not have one or more of the symptoms disclosed herein or elsewhere.

In some embodiments, the subject has been medically diagnosed as having PD by exhibiting clinical (e.g., physical) symptoms of the disease. In some embodiments, the subject exhibits one or more symptoms discussed herein, but does not exhibit all of the symptoms. Therefore, in some embodiments, the subject does not have one or more of the symptoms disclosed herein or elsewhere.

In some embodiments, the subject has been medically diagnosed as having PD by exhibiting clinical (e.g., physical) symptoms of the disease. In some patients the appearance of a sleep-related disorder precedes a clinical diagnosis of PD. Therefore, in some embodiments, the compounds or compositions disclosed herein are administered prior to a clinical diagnosis of PD.

c. Amyotrophic Lateral Sclerosis

The methods disclosed herein can be used to treat a subject with amyotrophic lateral sclerosis. Amyotrophic lateral sclerosis (ALS) is a fatal motor neuron disease, affecting both the first and second order motor neurons. The progression of ALS is characterized by a degeneration of motor neurons associated with a demyelination in the anterior horn of the spinal cord. The etiology is only partially understood. Of the 5-10% familial cases, 20% carry a mutation of the superoxide dismutase 1 (SOD1) gene. Such a mutation is also present in 5% of the sporadic cases (Rowland, et al., *New Engl J Med,* 44:1688-1700 (2001)). Three to four percent 3%-4% of familial cases are due to pathogenic variants in either the TDP-43 or FUS gene (Mackenzie, et al., *Lancet Neurol.,* 9:995-1007 (2010)).

In some embodiments, the subject exhibits one or more of the ALS clinical symptoms, one or more ALS molecular symptoms, or a combination thereof, such as those discussed herein and elsewhere. Clinical symptoms of ALS are known in the art. For example, the earliest symptoms of ALS are typically weakness and/or muscle atrophy. Other early symptoms include trouble swallowing, cramping, or stiffness of affected muscles; muscle weakness affecting an arm or a leg; and/or slurred and nasal speech, and in some cases dementia.

To be diagnosed with ALS, a patient must have signs and symptoms of both upper and lower motor neuron damage that cannot be attributed to other causes. The diagnosis depends on progressive degeneration of upper (UMN) and lower (LMN) motor neurons findings by history and examination and is accurate 95% of the time when made by an experienced clinician (Gordon, *Aging and Disease,* 4(5): 295-310 (2013)). Electromyography can be used to confirm widespread lower motor neuron disease and exclude other diseases such as multifocal motor neuropathy with conduction block. Brain and spinal MRI rule out conditions that affect the UMN, including cervical spondylosis. Occasionally the brain MRI shows bilateral signal changes within the corticospinal tracts, a finding that is pathognomonic of ALS. The El Escorial criteria help standardize diagnosis for clinical research studies (Brooks, et al., *Amyotroph Lateral Scler Other Motor Neuron Disord,* 1:293-299 (2000)).

Over time, patients experience increasing difficulty moving, swallowing (dysphagia), and speaking or forming words (dysarthria). Symptoms of upper motor neuron involvement include tight and stiff muscles (spasticity) and exaggerated reflexes (hyperreflexia) including an overactive gag reflex. An abnormal reflex commonly called Babinski's sign also indicates upper motor neuron damage. Symptoms of lower motor neuron degeneration include muscle weakness and atrophy, muscle cramps, and fleeting twitches of muscles that can be seen under the skin (fasciculations). Degeneration of bulbar upper motor neurons can cause exaggeration of motor expressions of emotion.

Progression is subject-specific, however, eventually most patients are not able to walk or use their hands and arms. They also lose the ability to speak and swallow their food, and most end on a portable ventilator. The rate of progression can be measured using an outcome measure called the "ALS Functional Rating Scale Revised (ALSFRS-R)", a 12-item instrument administered as a clinical interview or patient-reported questionnaire that produces a score between 48 (normal function) and 0 (severe disability).

A survey-based study amongst clinicians showed that they rated a 20% change in the slope of the ALSFRS-R would be clinically meaningful (Castrillo-Viguera, et al., *Amyotroph Lateral Scler,* 11(1-2):178-80 (2010)). Therefore, the composition can be administered to a subject an amount effective to change in the slope of the ALSFRS-R of a subject 1%, 5%, 10%, 15%, 20%, or more.

In some embodiments, the ALSFRS-R score of the subject is taken prior to, and one or more after initiation of treatment. In some embodiments, the ALSFRS-R score takes day, weeks, months, or more to improve.

In some embodiments, the subject exhibits one or more of the ALS clinical symptoms, one or more ALS molecular symptoms, or a combination thereof, such as those discussed herein and elsewhere. In some embodiments, the subject exhibits one or more symptoms discussed herein, but does not exhibit all of the symptoms. Therefore, in some embodiments, the subject does not have one or more of the symptoms disclosed herein or elsewhere.

In some embodiments, the subject has been medically diagnosed as having ALS by exhibiting clinical (e.g., physical) symptoms of the disease. In some embodiments, the subject exhibits one or more symptoms discussed herein, but does not exhibit all of the symptoms. Therefore, in some embodiments, the subject does not have one or more of the symptoms disclosed herein or elsewhere.

In some embodiments, the subject has been medically diagnosed as having ALS by exhibiting clinical (e.g., physical) symptoms of the disease. In some patients the appearance of sleep-related disorder precedes a clinical diagnosis of ALS. Therefore, in some embodiments, the compounds or compositions disclosed herein are administered prior to a clinical diagnosis of ALS. In some embodiments, a genetic test indicates that the subject has one or more genetic mutations associated with ALS.

d. Alzheimer's Disease

The methods disclosed herein can be used to treat a subject with Alzheimer's disease. Alzheimer's disease (AD) is the most common form of dementia. Although the cause and progression of AD are not entirely understood, research indicates plaques and tangles in the brain play a pathophysiological role. Current treatments only help with the symptoms of the disease and there are no available treatments that stop or reverse the progression of the disease.

In some embodiments, the subject exhibits one or more of the AD clinical symptoms, one or more AD molecular symptoms, or a combination thereof, such as those discussed herein and elsewhere. Clinical symptoms of AD are known in the art. Although Alzheimer's disease develops differently for every individual, there are many common symptoms. Early symptoms are often mistakenly thought to be "age-related" concerns, or manifestations of stress. One of the most common early symptoms is short term memory loss. Moderate stage symptoms can include, for example, increased memory loss and confusion, problems recognizing family and friends, continuously repeating stories, favorite wants, or motions, difficulty doing things that have multiple steps, like getting dressed, and/or lack of concern for hygiene and appearance. Severe stage symptoms can include, for example, inability to recognize oneself or family, inability to communicate, lack of control over bowel and bladder, groaning, moaning, or grunting, and/or needing help with all activities of daily living. Other common symptoms can include confusion, irritability, aggression, mood swings, trouble with language, and long-term memory loss. Gradually, bodily functions are lost, ultimately leading to death.

When AD is suspected, the diagnosis is usually confirmed with tests that evaluate behavior and thinking abilities (e.g., cognitive testing), often followed by a brain scan if available. Assessment of intellectual functioning including memory testing and neuropsychological tests such as the mini-mental state examination (MMSE) are widely used to evaluate the cognitive impairments needed for diagnosis (Waldemar, et al., *Eur J Neurol.* 14(1):e1-26 (2007)). Neurological examination in early AD will usually provide normal results, except for obvious cognitive impairment, which may not differ from that resulting from other diseases processes, including other causes of dementia.

Examination of brain tissue can lead to a definitive diagnosis. AD develops for an unknown and variable amount of time before becoming fully apparent, and it can progress undiagnosed for years.

In some embodiments, the subject exhibits one or more of the AD clinical symptoms, one or more ALS molecular symptoms, or a combination thereof, such as those discussed herein and elsewhere. In some embodiments, the subject exhibits one or more symptoms discussed herein, but does not exhibit all of the symptoms. Therefore, in some embodiments, the subject does not have one or more of the symptoms disclosed herein or elsewhere.

In some embodiments, the subject has been medically diagnosed as having AD by exhibiting clinical (e.g., physical) symptoms of the disease. In some embodiments, the subject exhibits one or more symptoms discussed herein, but does not exhibit all of the symptoms. Therefore, in some embodiments, the subject does not have one or more of the symptoms disclosed herein or elsewhere.

In some embodiments, the subject has been medically diagnosed as having AD by exhibiting clinical (e.g., physical) symptoms of the disease. In some patients the appearance of sleep-related disorder precede a clinical diagnosis of AD. Therefore, in some embodiments, the compounds or compositions disclosed herein are administered prior to a clinical diagnosis of AD.

e. Traumatic Brain Injury

In another particular embodiment, the disclosed compositions are used to treat a subject suffering from traumatic brain injury (TBI). Traumatic brain injury occurs when an external mechanical force, typically head trauma, causes brain dysfunction.

Traumatic brain injury can have wide-ranging physical and psychological effects. Some signs or symptoms may appear immediately after the traumatic event, while others may not appear until days or weeks later. Symptoms of TBI include, but are not limited to, loss of consciousness; a state of being dazed, confused or disoriented; memory or concentration problems; headache, dizziness or loss of balance; nausea or vomiting; sensory problems such as blurred vision, ringing in the ears or a bad taste in the mouth; sensitivity to light or sound; mood changes or mood swings; feeling depressed or anxious; fatigue or drowsiness; difficulty sleeping; sleeping more than usual, agitation, combativeness or other unusual behavior; slurred speech; inability to awaken from sleep; weakness or numbness in fingers and toes; loss of coordination; convulsions or seizures, dilation of one or both pupils of the eyes; and/or clear fluids draining from the nose or ears. In children, additional symptoms include change in eating or nursing habits; persistent crying and inability to be consoled; unusual or easy irritability; change in ability to pay attention; change in sleep habits; sad or depressed mood; and/or loss of interest in favorite toys or activities.

TBI can be diagnosed using the Glasgow Coma Scale, a 15-point test that helps a doctor or other emergency medical personnel assess the initial severity of a brain injury by checking a person's ability to follow directions and move their eyes and limbs. The coherence of speech also provides important clues. Abilities are scored numerically with higher scores indicating more mild injury. Imaging such as computerized tomography (CT) and magnetic resonance imaging (MRI), as well as intracranial pressure monitoring can also be used to assist in the diagnoses by helping to identify the local(s) and extent of the trauma.

Conventional treatments for TBI include administration of agents such as diuretics, anti-seizure drugs, and coma-inducing drugs; surgery to remove clotted blood, repair skull fractures, and/or relieve pressure inside the skull.

IV. Methods of Increasing Tonic Inhibition

Method of using 4,5,6,7-tetrahydroisoxazolo(5,4-c)pyridin-3-ol (THIP), a derivative thereof, or a pharmaceutically acceptable salt thereof for increasing tonic inhibition are also provided. The methods can be used to increase tonic inhibition in a subject with a disease or disorder characterized by a defect or deficiency in tonic inhibition. Exemplary diseases include neurogenetic diseases such as Fragile X syndrome or Angelman syndrome.

A. Treatment Protocol

1. Tonic Inhibition

The disclosed methods for increasing tonic inhibition in a subject typically include administering to a subject in need thereof an effective amount of THIP or a derivative thereof to increase tonic inhibition in the brain of the subject.

Neural inhibition in the mammalian brain is mediated by two fast transmitters, glycine and gamma-aminobutyric acid (GABA) (Jonas and Buzaki, Scholarpedia, 2(9):3286 (2007)). Glycine is the major inhibitory transmitter in the spinal cord, while GABA is the major transmitter in higher brain regions. GABA released from presynaptic terminals can activate three different types of receptors: GABA receptors (GABARs) type A, B, and C. Neural inhibition can be "phasic" or "tonic". Phasic inhibition is a short-lasting inhibition most often generated by the activation of GABAA receptors following action potentials in a presynaptic interneuron. Among several long-lasting forms of inhibition is tonic GABAA conductance activated by ambient GABA in the extracellular space. Tonic inhibition is mediated by molecularly and functionally specialized GABAA receptors containing alpha6 or delta subunits, and which display a high affinity for GABA binding. THIP, is a superagonist of the δ-subunit-containing presynaptic and extrasynaptic GABA A receptors that mediates strong tonic inhibitory conductance in the CNS (Brown, et al., *Br. J Pharmacol.*, 136:965-974 (2002), Glykys, et al., *J Physiol.*, 582:1163-1178 (2007), Brown, et al., *Cell*, 107:477-487 (2001).

Therefore, THIP can be used to increase tonic inhibition is a subject in need thereof.

In vitro and animal model studies show that reduced tonic inhibition can be an underlying cause of some neurogenetic diseases. For example, studies show that decreased concentrations of GABA can lead to decreased tonic inhibition of cerebellar granule cells which is the underlying cause of cerebellar ataxia in Angelman syndrome (Egawa, et al., *Science Translational Medicine*, 4:163ra157 (2012)). Treatment with THIP (500 nM) increased tonic holding currents and reduced the excitability of cerecellar ganule cells from a mouse model of Angelman syndrome rescuing the defect. Doses of THIP (1.25 mg/kg and 2.5 mg/kg) were effective to rescue cerebellar dysfunction in vivo (reduced hind paw abduction without effective width or stride), while low effective doses (e.g., 1.25 mg/kg) were effective to rescue cerebellar dysfunction without adverse effects (reduced time on rotarod).

Studies also show that impaired GABAergic transmission in different brain regions such as the amygdala, striatum, or cerebral cortex contributes to neuron excitability deficits and behavioral abnormalities in Fragile X syndrome (Olmos-Serrano, et al., Dev. Neurosci., 33:395-403 (2011), Olmos-Serrano, et al., *J. Neurosci.*, 30(29):9929-9938 (2010), Braat and Kooy, Drug Discovery Today, 19(4):510-519 (2014)). In vitro experiments reveled that augmentation of tonic inhibitory tone using THIP rescued the decreased bioavailability of GABA and reduced tonic currents of principal neurons of the BL amygdala of Fmr1 knockout mice. Furthermore, THIP treatment improved a number of Fragile X phenotypes in Fmr1 knockout mice in vivo, including, reduction or dampening of hyperactivity (e.g., measured by travel and velocity), and reduction of hypersensitivity to auditory stimuli.

2. Dosage and Administration

The disclosed methods of increasing tonic inhibition typically include administering a subject in need thereof an effective amount of THIP or a derivative thereof, preferably is a pharmaceutically acceptable composition such as those discussed in more detail above.

The effective amount or therapeutically effective amount is typically a dosage sufficient to increase tonic inhibition of neurons in the brain of the subject. In some embodiment the method reduces or prevents one or more neuropsychiatric morbidities or phenotypes in a subject with a neurogenetic disease or disorder as discussed in more detail below. Therefore, the amount can be effective to treat or prevent one or more symptoms of a neurogenetic disease, or to otherwise provide a desired pharmacologic and/or physiologic effect, for example.

The precise dosage will vary according to a variety of factors such as subject-dependent variables (e.g., age, immune system health, clinical symptoms etc.). Exemplary dosages, symptoms, pharmacologic, and physiologic effects are discussed in more detail below.

Particularly preferred embodiments include formulations for extended release. For example, the formulation can suitable for administration once daily or less. In some embodiments, the composition is only administered to the subject once every 24-48 hours.

The timing of the administration of the composition will depend on the formulation and/or route of administration used. In some embodiments, administration of the composition will be given as a long-term treatment regimen whereby pharmacokinetic steady state conditions will be reached.

A preferred route of administration is transdermal, for example, a transdermal patch that is contacted with the skin of the subject.

In general, by way of example only, dosage forms useful in the disclosed methods can include doses in the range of 0.1 to 1,000 mg, 1 to 200 mg, 5 to 175 mg, 7.5 to 150 mg, or 10 to 125 mg, or 12.5 to 150 mg, or 15 to 125 mg, or 17.5 to 100 mg, or 20 to 75 mg, or 22.5 to 60 mg, or 25 to 50 mg, with doses of 1 mg, 5 mg, 10 mg, 15 mg, 20 mg, 25 mg, 30 mg, 35 mg, 40 mg, 45 mg, 50 mg, 55 mg, 60 mg, 75 mg, and 100 mg being specific examples of preferred doses. Typically, such dosages are administered once, twice, or three times daily, or every other day to a human.

A typical oral dose form preferably includes from about 2.5 mg to about 30 mg THIP. Preferably, the THIP is in a crystalline form. Further embodiments of the medicament comprises an effective amount of THIP from 2.5 mg to 20 mg, such as 2.5 mg to 4 mg, 4 mg to 6 mg, 6 mg to 8 mg, 8 mg to 10 mg, 10 mg to 12 mg, 12 mg to 14 mg, 14 mg to 16 mg, 16 mg to 18 mg, or 18 mg to 20 mg, e.g. 2.5 mg, 5 mg, 7.5 mg, 10 mg, 12.5 mg, 15 mg, 17.5 mg, or 20 mg. A typical embodiment is about 5 mg to about 20 mg of crystalline THIP, such as the hydrochloride of THIP. Typically, such dosages are administered once, twice, or three times daily, or every other day to a human. In some embodiments, the total amount administered to a subject in 24 hour period is 1 mg to 50 mg. In some embodiments, the subject is started at a low dose and the dosage is escalated in the drug is well tolerated in the subject.

In the most preferred embodiments, the dosage is effective to increase tonic inhibition without causing an adverse effect in the subject. Adverse effects can include, for example, induced neuronal dysfunction and negative effects on the function of thalamo-cortical network, such as increased frequency of seizures or excessive drowsiness or daytime somnolence. The animals models discussed above utilize a dosage of 1.25 mg/kg to 3 mg/kg in mice. In a particular animal model, a dosage of 1.25 mg/kg was preferred over a dosage of 2.5 mg/kg because there were fewer adverse effects. Therefore in some embodiments, the dosage is about 0.1 mg/kg to about 5 mg/kg, preferably wherein there are few or no adverse effects. Dosages can be scaled from mouse to human using conversions that are known in the art. Because this therapy typically includes administration during a time when the subject is active, the dosage also preferably does not induce a sedative effect in the subject.

In some embodiments, the effect of the composition on a subject is compared to a control. For example, the effect of the composition on a particular symptom, pharmacologic, or physiologic indicator can be compared to an untreated subject, or the condition of the subject prior to treatment. In some embodiments, the symptom, pharmacologic, or physiologic indicator is measured in a subject prior to treatment, and again one or more times after treatment is initiated. In some embodiments, the control is a reference level, or average determined based on measuring the symptom, pharmacologic, or physiologic indicator in one or more subjects that do not have the disease or condition to be treated (e.g., healthy subjects). In some embodiments, the effect of the treatment is compared to a conventional treatment that is known the art, such as one of those discussed herein.

B. Conditions, Symptoms, Subjects, and Diseases to be Treated

In some embodiments, subjects in need of tonic inhibition are subjects with a neurogenetic disease. In some embodiments, the composition is administered in an effective amount to reduce or prevent one or more symptoms or phenotypes of the disease. Diseases and symptoms thereof are discussed in more detail below.

1. Angelman Syndrome

In some embodiments, the composition is used to treat a subject with Angelman syndrome. Angelman syndrome is a neurogenetic disorder caused by deletion or inactivation of genes on the maternally inherited chromosome 15 while the paternal copy, which may be of normal sequence, is imprinted and silenced. Prader-Willi syndrome, is caused by a similar loss of paternally inherited genes and maternal imprinting.

Symptoms of Angelman syndrome include: consistent symptoms which are exhibited in 100% of cases, frequent symptoms which occur in more than 80% of cases, and associated which occur in 20-80% of cases. Consistent symptoms include developmental delay; speech impairment, no or minimal use of words; receptive and non-verbal communication skills higher than verbal ones; movement or balance disorder; usually ataxia of gait and/or tremulous movement of limbs; and behavioral uniqueness such as frequent laughter/smiling, apparent happy demeanor, easily excitable personality, often with hand flapping movements, hypermotoric behavior, short attention span, or any combination thereof. Frequent symptoms include delayed, disproportionate growth in head circumference, usually resulting in microcephaly (absolute or relative) by age 2; seizures, onset usually <3 years of age; and abnormal EEG having a characteristic pattern with large amplitude slow-spike waves. Associated symptoms include strabismus; hypopigmented skin and eyes; tongue thrusting; suck/swallowing disorders; hyperactive tendon reflexes; feeding problems during infancy; uplifted, flexed arms during walking; prominent mandible; increased sensitivity to heat; wide mouth, wide-spaced teeth; sleep disturbance; frequent drooling, protruding tongue; attraction to/fascination with water; excessive chewing/mouthing behaviors; flat back of head; smooth palms; attraction to/fascination with water; fascination with crinkly items such as certain papers and plastics; abnormal food related behaviors; obesity (in the older child); scoliosis; and constipation.

Other common symptoms of Angelman syndrome as well as methods of diagnoses are discussed in Williams, et al., *American Journal of Medical Genetics,* 140A:413-418 (2006), which is specifically incorporated by referenced herein in its entirety.

2. Fragile X Syndrome

In some embodiments, the composition is used to treat a subject with Fragile X syndrome (FXS). Fragile X syndrome is a neurogenetic disorder. It is the most common single-gene cause of autism and an inherited cause of intellectual disability especially among boys. FXS is related to the expansion of the CGG trinucleotide repeat affecting the Fragile X mental retardation 1 (FMR1) gene on the X chromosome. In normal individuals, this DNA segment is repeated from 5 to about 40 times. In people with fragile X syndrome, the CGG segment is repeated more than 200 times, which leads to silencing of the gene. Loss or a shortage (deficiency) of FMR1 disrupts nervous system functions and leads to the signs and symptoms of fragile X syndrome.

In addition to intellectual disability, prominent characteristics and symptoms of the syndrome can include an elongated face, large or protruding ears, flat feet, larger testes (macroorchidism), and low muscle tone; recurrent otitis media (middle ear infection) and sinusitis is common during early childhood; speech may be cluttered or nervous; stereotypic movements (e.g., hand-flapping) and atypical social development, particularly shyness, limited eye contact, memory problems, and difficulty with face encoding; psychiatric problems including attention deficit hyperactive disorder, obsessive-compulsive disorder, mood disorders, dementia, and anxiety disorders; hypersensitivity and repetitive behavior including very short attention spans, hyperactivity, and hypersensitivity to visual, auditory, tactile, and olfactory stimuli, and perseveration; ophthalmologic problems such as strabismus and amblyopia; neurological complications such as seizures; problems in performing tasks that require the central executive of working memory; and premature menopause. Some individuals with fragile X syndrome also meet the diagnostic criteria for autism.

Diagnosis of fragile X syndrome is made through genetic testing to determine the number of CGG repeats. Although at least 200 repeats are needed for a diagnosis of FXS, males and females with 55 to 200 repeats of the CGG segment are said to have an FMR1 gene premutation. Most people with a premutation are intellectually normal, however, some individuals with a premutation have lower than normal amounts of FMRP. As a result, they may have mild versions of the physical symptoms of the disease and may experience emotional problems such as anxiety or depression.

In some embodiments, the subject has Fragile X—associated tremor/ataxia syndrome (FXTAS).

3. Rett Syndrome

In some embodiments, the composition is used to treat a subject with Rett Syndrome, also referred to as cerebroatrophic hyperammonemia. Rett syndrome is a neurodevelopmenal disorder that most often affects females. Genetically, Rett syndrome is most typically caused by a mutation in the gene MECP2 located on the X chromosome. The mutation can arise sporadically or from germline mutations, but is not typically inherited. In less than 10% of Rett syndrome cases, mutations in the genes CDKL5 or FOXG1 have also been found. Rett syndrome is initially diagnosed by clinical observation, but the diagnosis is definitive when there is a genetic defect in the MECP2 gene.

The onset and severity of Rett syndrome vary from subject to subject. Before the onset of symptoms, the child generally appears to grow and develop normally. Early subtle abnormalities even in early infancy, can include loss of muscle tone (hypotonia), difficulty feeding, and jerkiness in limb movements. Next, gradually, mental and physical symptoms begin to manifest. The subject loses purposeful use of her hands and the ability to speak, and can experience other early symptoms including problems crawling or walking and diminished eye contact. The loss of functional use of the hands is followed by compulsive hand movements such as wringing and washing. Apraxia, the inability to perform motor functions, can interfere with all body movements, including eye gaze and speech.

Children with Rett syndrome can also exhibit autistic-like behaviors such as incontinence, screaming fits, inconsolable crying, breath holding, hyperventilation & air swallowing, avoidance of eye contact, lack of social/emotional reciprocity, markedly impaired use of nonverbal behaviors to regulate social interaction, loss of speech, and sensory problems. Other symptoms include walking on the toes, sleep problems, a wide-based gait, teeth grinding and difficulty chewing, slowed growth, seizures, cognitive disabilities, and apnea (breath holding), possible short stature, sometimes with unusual body proportions because of difficulty walking or malnutrition caused by difficulty swallowing, hypotonia, delayed or absent ability to walk, ataxia, microcephaly, gastrointestinal problems, some forms of spasticity, chorea, and dystonia.

There is currently no cure for Rett syndrome, but restoration of MECP2, for example using Insulin-like Growth Factor-1 (IGF-1) has shown promise in a mouse model (Tropea, et al., *Proc Natl Acad Sci USA.*, 106(6): 2029-2034 (2009)). NMDA receptor antagonists have also shown promise. Symptoms can also be treated using, for example, sleep aids, selective serotonin reuptake inhibitors (SSRIs), antipsychotics (for self-harming behaviors), beta-blockers (for long QT syndrome), and agents to manage gastrointestinal dysfunction and malnutrition.

4. Autism Spectrum Disorders

In some embodiments, the composition is used to treat a subject with Asperger's syndrome, pervasive developmental disorder, not otherwise specified (PDD-NOS), autistic disorder, or another autism spectrum disorder.

Autism spectrum disorder (ASD) is a range of neurodevelopment disorders, generally characterized by social impairments, communication difficulties, and restricted, repetitive, and stereotyped patterns of behavior. Autistic disorder, also referred to as autism or classical ASD, is the most severe form of ASD. Children with classic ASD exhibit impairments involving social and language function as well as repetitive behaviors that are typically more severe than in children with other spectrum disorders. Often, they also have mental retardation and/or seizures.

Other conditions along the autism spectrum include Asperger syndrome, and PDD-NOS. Asperger's syndrome (AS) is the mildest form of autism. Children with AS become obsessively interested in a single object or subject. They often learn all about their preferred subject and discuss it continuously. Social skills are typically markedly impaired in AS children, and they are often awkward and uncoordinated.

Symptoms of PDD-NOS can vary widely from one child to the next. Overall, child with PDD-NOS can be characterized as having impaired social interaction, better language skills than kids with autistic disorder but not as good as those with Asperger's syndrome, fewer repetitive behaviors than children with Asperger's syndrome or autistic disorder, and a later age of onset. There are no agreed-upon criteria for diagnosing a subject with PDD-NOS. A child can be diagnosed with PDD-NOS if the child seems autistic to professional evaluators but does not meet all the criteria for autistic disorder.

Pharmaceutical interventions typically limited to treatment of specific autism-related symptoms, such as anxiety, depression, or obsessive-compulsive disorder. Antipsychotic medications can be used to treat behavioral problems. Seizures can be treated with one or more anticonvulsant drugs. Medication used to treat attention deficit disorder can be used reduce impulsivity and hyperactivity in autism spectrum subjects.

V. Combination Therapies

In some embodiments, THIP or a derivative thereof is administered in combination with one or more additional active agents. The combination therapies can include administration of the active agents together in the same admixture, or in separate admixtures. Therefore, in some embodiments, the pharmaceutical composition includes two, three, or more active agents. Such formulations typically include an effective amount of THIP or a derivative. The different active agents can have the same, or different mechanisms of action. In some embodiments, the combination results in an additive effect on the treatment of the disease or disorder. In some embodiments, the combinations results in a more than additive effect on the treatment of the disease or disorder.

The pharmaceutical compositions can be formulated as a pharmaceutical dosage unit, also referred to as a unit dosage form.

A THIP or a derivative can be the singular active agent administered to increase slow wave sleep, to increase tonic inhibition, to treat a neurogenetic disorder, a neurodegenerative disease, a central nervous system disorder, or a symptom or pathology thereof; or THIP or a derivative thereof can be administered in combination with another agent increase slow wave sleep, to reduce or prevent cognitive impairment, to treat a neurodegenerative disease, a central nervous system disorder, or a symptom or pathology thereof.

In particular embodiments, a combination therapy includes THIP or a derivative thereof and one or more conventional treatments for neurodegeneration, or for increasing or enhancing neuroprotection, such as those discussed herein. Exemplary neuroprotective agents are known in the art and include, for example, glutamate antagonists, antioxidants, and NMDA receptor stimulants. Other neuroprotective agents and treatments include caspase inhibitors, trophic factors, anti-protein aggregation agents, therapeutic hypothermia, and erythropoietin. In some embodiments, THIP or derivative thereof is administered to a subject in combination with a treatment that increase nerve regeneration.

In a particular embodiment, THIP or a derivative thereof is administered to a subject in combination with a conventional treatment for Huntington's disease, such as a dopamine blocker to help reduce abnormal behaviors and movements, or a drug such as amantadine and tetrabenazine to control movement, etc. Other drugs that help to reduce chorea include neuroleptics and benzodiazepines. Compounds such as amantadine or remacemide have shown preliminary positive results. Hypokinesia and rigidity, especially in juvenile cases, can be treated with antiparkinsonian drugs, and myoclonic hyperkinesia can be treated with valproic acid. Psychiatric symptoms can be treated with medications similar to those used in the general population. Selective serotonin reuptake inhibitors and mirtazapine have been recommended for depression, while atypical antipsychotic drugs are recommended for psychosis and behavioral problems.

In another particular embodiment, THIP or a derivative thereof is administered to a subject in combination with a conventional treatment for Parkinson's disease, such as levodopa (usually combined with a dopa decarboxylase inhibitor or COMT inhibitor), a dopamine agonist, or an MAO-B inhibitor. Other common agents that can be used in combination the disclosed combinations include amantadine and anticholinergics for treating motor symptoms, clozapine for treating psychosis, cholinesterase inhibitors for treating dementia, and modafinil for treating daytime sleepiness.

In another particular embodiment, THIP or a derivative thereof is administered to a subject in combination with a conventional treatment for ALS such as the antiexcitotoxin riluzole (RILUTEK®) (2-amino-6-(trifluoromethoxy) benzothiazole). Other medications, most used off-label, and interventions can reduce symptoms due to ALS. Some treatments improve quality of life and a few appear to extend life. Common ALS-related therapies are reviewed in Gordon, *Aging and Disease*, 4(5):295-310 (2013), which is specifically incorporated by reference herein in its entirety. Exemplary ALS treatments and interventions are provided in Table 1, below, which is adapted from Gordon, *Aging and Disease*, 4(5):295-310 (2013).

TABLE 1

Treatments for ALS

| Treatment | Administration | Indication |
|---|---|---|
| *Riluzole | 50 mg bid | ALS |
| *Multidisciplinary care | Every three monthly visits | All symptoms of ALS |
| *Non-invasive ventilation | Nighttime and during symptoms at least 4 hours/day | Respiratory insufficiency |
| Gastrostomy | Daily calorie supplements | Dysphagia and malnutrition |
| *Dextromethorphan/ quinidine | 20 mg/10 mg bid | Pseudobulbar affect |
| Diaphragm Pacing | Up to 24 hours/day | Respiratory insufficiency |
| Brain-computer interface | Experimental | Communication |
| Amitriptyline | 12.5-125 mg qhs | Anxiety |
| SSRI antidepressants | 20-100 mg qd | |
| Mirtazapine | 15-30 mg qhs | |
| Buspirone | 10 mg tid | |
| Diazepam | 2-10 mg tid | |
| Lorazepam | 0.5-2 mg tid | |
| Mirtazapine | 15-30 mg qhs | |
| SSRI antidepressants | 10-100 mg qd | |
| Diazepam | 2-10 mg tid | Cramps |
| Phenytoin | 100-300 mg qhs | |
| Vitamin E | 400 IU tid | |
| Mirtazapine | 15-30 mg qhs | Depression |
| SSRI antidepressants | 20-100 mg qd | |
| Tricyclic antidepressants | 12.5-150 mg qhs | |
| Venlafaxine | 37.5-75 mg qd | |
| Amantadine | 100 mg qAM, qnoon | Fatigue |
| Bupropion SR | 150-450 mg qd | |
| Fluoxetine | 20-80 mg qd | |
| Pemoline | 18.75-93.75 mg qd | |
| Pyridostigmine | 60 mg tid | |
| Venlafaxine | 75-225 mg qd | |
| Amitriptyline | 12.5-125 mg qhs | Sialorrhea |
| Atropine sulphate | 0.4 mg q4-6 h 1-2 ophthalmic drops SL q4-6 h | |
| Diphenhydramine | 25-50 mg tid | |
| Hyoscyamine sulfate | 0.125-0.25 mg q4 h | |
| Scopolamine transdermal patch | 0.5 mg q72 h | |
| Baclofen | 10-60 mg tid | Spasticity |
| Benzodiazepines | 2-10 mg tid | |
| Dantrolene | 25-100 mg tid | |
| Tizanidine | 2-8 mg tid | |
| Amitriptyline | 12.5-75 mg qhs | Urinary urgency |
| Oxybutynin | 2.5-5 mg bid 3.9 mg patch qd | |
| Tolterodine | 1-2 mg bid | |

Bid = twice daily; IU = international units; qAM = every morning; qd = daily; qhs = every day; qt = bedtime; qid = four times daily; qnoon = every day at noon; qxh = every x hours; SL = sublingual; SR = slow release; SSRI = serotonin-specific reuptake inhibitor; tid = three times daily.
*shown to have a beneficial effect in ALS A number of other agents have been tested in one or more clinical trials with efficacies ranging from non-efficacious to promising. Exemplary agents are reviewed in Carlesi, et al., *Archives Italiennes de Biologie*, 149:151-167 (2011). For example, in some embodiments, THIP or a derivative thereof, is administered to a subject in combination with an agent that reduces excitotoxicity such as talampanel (8-methyl-7H-1,3-dioxolo(2,3)benzodiazepine), a cephalosporin such as ceftriaxone, or memantine; an agent that reduces oxidative stress such as coenzyme Q10, manganoporphyrins, KNS-760704 [(6R)-4,5,6,7-tetrahydro-N6-propyl-2,6-benzothiazole-diamine dihydrochloride, RPPX], or edaravone (3-methyl-1-phenyl-2-pyrazolin-5-one, MCI-186); an agent that reduces apoptosis such as histone deacetylase (HDAC) inhibitors including valproic acid, TCH346 (Dibenzo(b,f)oxepin-10-ylmethyl-methylprop-2-ynylamine), minocycline, or tauroursodeoxycholic Acid (TUDCA); an agent that reduces neuroinflammation such as thalidomide and celastol; a neurotropic agent such as insulin-like growth factor 1 (IGF-1) or vascular endothelial growth factor (VEGF); a heat shock protein inducer such as arimoclomol; or an autophagy inducer such as rapamycin or lithium.

In another particular embodiment, THIP or a derivative thereof is administered to a subject in combination with a conventional treatment for AD, for example, acetylcholinesterase inhibitor such as tacrine, rivastigmine, galantamine or donepezil; or an NMDA receptor antagonist such as memantine, or an antipsychotic drug.

In some embodiments, the active agent(s) is administered in combination with a co-therapy such as dietary changes with or without dietary supplements, exercise, psychological and/or psychosocial counseling, physical therapy, occupational therapy, and speech therapy.

Unless defined otherwise, all technical and scientific terms used herein have the same meanings as commonly understood by one of skill in the art to which the disclosed invention belongs. Publications cited herein and the materials for which they are cited are specifically incorporated by reference.

Those skilled in the art will recognize, or be able to ascertain using no more than routine experimentation, many equivalents to the specific embodiments of the invention described herein. Such equivalents are intended to be encompassed by the following claims.

I claim:

1. A method of treating Fragile X syndrome comprising administering to a patient in need thereof 4,5,6,7-tetrahydroisoxazolo(5,4-c)pyridin-3-ol (THIP) or a pharmaceutically acceptable salt thereof in an amount of less than 15 mg.

2. The method of claim 1, wherein the patient is administered 10 mg of THIP or a pharmaceutically acceptable salt thereof.

3. The method of claim 1, wherein the patient is administered 5 mg of THIP or a pharmaceutically acceptable salt thereof.

4. The method of claim 1, wherein the total amount of THIP or a pharmaceutically acceptable salt thereof administered to the patient in a 24-hour period is between less than 15 mg.

5. The method of claim 4, wherein the amount of the THIP or a pharmaceutically acceptable salt thereof administered in a 24-hour period is 10 mg.

6. The method claim 1, THIP or a pharmaceutically acceptable salt thereof is administered twice daily.

* * * * *